US008195273B2

(12) United States Patent
Trequattrini et al.

(10) Patent No.: US 8,195,273 B2
(45) Date of Patent: Jun. 5, 2012

(54) MAGNETIC RESONANCE IMAGING APPARATUS

(75) Inventors: Alessandro Trequattrini, Genoa (IT); Fabio Rezzonico, Como (IT); Eugenio Biglieri, Masio (IT); Luigi Satragno, Genoa (IT)

(73) Assignee: ESAOTE S.p.A., Milan (IT)

( * ) Notice: Subject to any disclaimer, the term of this patent is extended or adjusted under 35 U.S.C. 154(b) by 1784 days.

(21) Appl. No.: 10/768,169

(22) Filed: Feb. 2, 2004

(65) Prior Publication Data
US 2005/0187459 A1    Aug. 25, 2005

(51) Int. Cl.
*A61B 5/055* (2006.01)
(52) U.S. Cl. .......................... 600/415; 600/410
(58) Field of Classification Search .................. 600/407, 600/410, 415; 324/318–320; 5/601
See application file for complete search history.

(56) References Cited

U.S. PATENT DOCUMENTS

| | | |
|---|---|---|
| 4,534,076 A | 8/1985 | Barge |
| 4,651,099 A | 3/1987 | Vinegar et al. |
| 4,707,663 A | 11/1987 | Minkoff et al. |
| 4,734,646 A | 3/1988 | Shenoy et al. |
| 4,737,713 A | 4/1988 | Danby et al. |
| 4,766,378 A | 8/1988 | Danby et al. |
| 4,770,182 A | 9/1988 | Damadian et al. |
| 4,805,626 A | 2/1989 | Di Massimo et al. |
| 4,875,485 A | 10/1989 | Matsutani |
| 4,887,038 A | 12/1989 | Votruba et al. |
| 4,975,411 A | 12/1990 | Danby et al. |
| 4,985,678 A | 1/1991 | Gangarosa et al. |
| 4,990,850 A | 2/1991 | Votruba |
| 5,016,638 A | 5/1991 | Hsieh |
| 5,050,605 A | 9/1991 | Eydelman et al. |
| 5,061,897 A | 10/1991 | Danby et al. |
| 5,124,651 A | 6/1992 | Danby et al. |
| 5,153,546 A | 10/1992 | Laskaris |
| 5,305,749 A | 4/1994 | Li et al. |
| 5,436,607 A | 7/1995 | Chari et al. |
| 5,438,263 A | 8/1995 | Dworkin et al. |
| 5,490,513 A | 2/1996 | Damadian et al. |
| 5,495,171 A | 2/1996 | Danby et al. |
| 5,515,863 A | 5/1996 | Damadian |
| 5,575,287 A | 11/1996 | Eydelman |

(Continued)

FOREIGN PATENT DOCUMENTS
JP    1-242056    9/1989

OTHER PUBLICATIONS
US 6,204,666, 03/2001, Damadian et al. (withdrawn)

*Primary Examiner* — Tse Chen
*Assistant Examiner* — Peter Luong
(74) *Attorney, Agent, or Firm* — Buchanan Ingersoll & Rooney PC

(57) ABSTRACT

A magnetic resonance imaging apparatus including a magnetic structure having two opposite and spaced apart poles and a column or wall transverse to the poles and connecting the poles; the poles defining two opposite walls delimiting a patient-imaging space, the two opposite walls extending along substantially parallel planes which are substantially parallel to a vertical plane; and a patient positioning table which is slidably connected to a supporting frame between the two poles; the table being positioned with its longitudinal axis substantially parallel to the two opposite parallel walls of the poles and the table being oriented with its transverse axis perpendicular to at least one of the two opposite walls.

21 Claims, 15 Drawing Sheets

U.S. PATENT DOCUMENTS

| | | |
|---|---|---|
| 5,576,622 A | 11/1996 | Morrone et al. |
| 5,583,438 A | 12/1996 | Eydelman et al. |
| 5,583,439 A | 12/1996 | Danby et al. |
| 5,585,721 A | 12/1996 | Datsikas |
| 5,592,089 A | 1/1997 | Danby et al. |
| 5,606,970 A | 3/1997 | Damadian |
| 5,623,927 A | 4/1997 | Damadian et al. |
| 5,647,361 A | 7/1997 | Damadian |
| 5,664,569 A | 9/1997 | Damadian et al. |
| 5,689,190 A | 11/1997 | Cuppen |
| 5,694,935 A | 12/1997 | Damadian |
| 5,724,970 A | 3/1998 | Votruba et al. |
| 5,754,085 A | 5/1998 | Danby et al. |
| 5,760,582 A | 6/1998 | Morrone |
| 5,772,595 A | 6/1998 | Votruba et al. |
| 5,779,637 A | 7/1998 | Palkovich et al. |
| 5,810,006 A | 9/1998 | Votruba et al. |
| 5,841,278 A | 11/1998 | Green et al. |
| 5,899,859 A | 5/1999 | Votruba et al. |
| 5,939,883 A | 8/1999 | Green et al. |
| 5,952,734 A | 9/1999 | Gelbien |
| 5,983,424 A | 11/1999 | Naslund |
| 5,992,006 A | 11/1999 | Datsikas |
| 6,011,396 A | 1/2000 | Eckels et al. |
| 6,014,070 A | 1/2000 | Danby et al. |
| 6,023,165 A | 2/2000 | Damadian et al. |
| 6,023,166 A | 2/2000 | Eydelman |
| 6,025,717 A | 2/2000 | Hertz et al. |
| 6,028,429 A | 2/2000 | Green et al. |
| 6,037,775 A | 3/2000 | Shenoy et al. |
| 6,075,364 A | 6/2000 | Damadian et al. |
| D427,685 S | 7/2000 | Danby et al. |
| D428,151 S | 7/2000 | Danby et al. |
| 6,107,974 A | 8/2000 | Votruba et al. |
| 6,149,790 A | 11/2000 | Oikawa et al. |
| 6,150,820 A | 11/2000 | Damadian et al. |
| 6,157,194 A | 12/2000 | Vassallo et al. |
| 6,165,139 A | 12/2000 | Damadian |
| 6,201,394 B1 | 3/2001 | Danby et al. |
| 6,208,145 B1 | 3/2001 | Danby et al. |
| 6,225,805 B1 | 5/2001 | Damadian et al. |
| 6,229,310 B1 | 5/2001 | Green et al. |
| 6,249,695 B1 | 6/2001 | Damadian |
| 6,280,383 B1 | 8/2001 | Damadian et al. |
| 6,288,546 B1 | 9/2001 | Damadian et al. |
| 6,323,749 B1 | 11/2001 | Hsieh |
| 6,335,623 B1 | 1/2002 | Damadian et al. |
| 6,346,816 B1 | 2/2002 | Damadian et al. |
| 6,366,094 B1 | 4/2002 | Vassallo et al. |
| 6,369,571 B1 | 4/2002 | Damadian et al. |
| 6,373,251 B1 | 4/2002 | Damadian et al. |
| 6,385,481 B2 | 5/2002 | Nose et al. |
| 6,400,156 B1 | 6/2002 | Damadian et al. |
| 6,400,157 B1 | 6/2002 | Bonanni et al. |
| 6,404,202 B1 | 6/2002 | Damadian et al. |
| 6,414,490 B1 | 7/2002 | Damadian et al. |
| 6,424,854 B2 | 7/2002 | Hayashi et al. |
| 6,437,571 B1 | 8/2002 | Danby et al. |
| 6,445,185 B1 | 9/2002 | Damadian et al. |
| 6,445,186 B1 | 9/2002 | Damadian et al. |
| 6,456,075 B1 | 9/2002 | Damadian et al. |
| 6,469,508 B1 | 10/2002 | Damadian et al. |
| 6,496,007 B1 | 12/2002 | Damadian et al. |
| 6,504,371 B1 | 1/2003 | Damadian et al. |
| 6,504,462 B1 | 1/2003 | Datsikas |
| 6,507,192 B1 | 1/2003 | Damadian et al. |
| 6,522,145 B1 | 2/2003 | Damadian et al. |
| 6,541,973 B1 | 4/2003 | Danby et al. |
| 6,544,041 B1 | 4/2003 | Damadian |
| 6,549,009 B1 | 4/2003 | Hertz et al. |
| 6,566,991 B1 | 5/2003 | Rimkunas et al. |
| 6,583,696 B1 | 6/2003 | Datsikas |
| 6,591,202 B1 | 7/2003 | Rimkunas et al. |
| 6,617,852 B1 | 9/2003 | Danby et al. |
| 6,621,267 B1 | 9/2003 | Damadian et al. |
| 6,621,433 B1 | 9/2003 | Hertz |
| 6,634,088 B1 | 10/2003 | Morrone |
| 6,636,040 B1 | 10/2003 | Eydelman |
| 6,677,753 B1 | 1/2004 | Danby et al. |
| 6,860,272 B2 * | 3/2005 | Carter et al. ................... 128/870 |
| 6,934,574 B1 * | 8/2005 | Damadian et al. ............ 600/415 |
| 2003/0204136 A1 | 10/2003 | Green et al. |

* cited by examiner

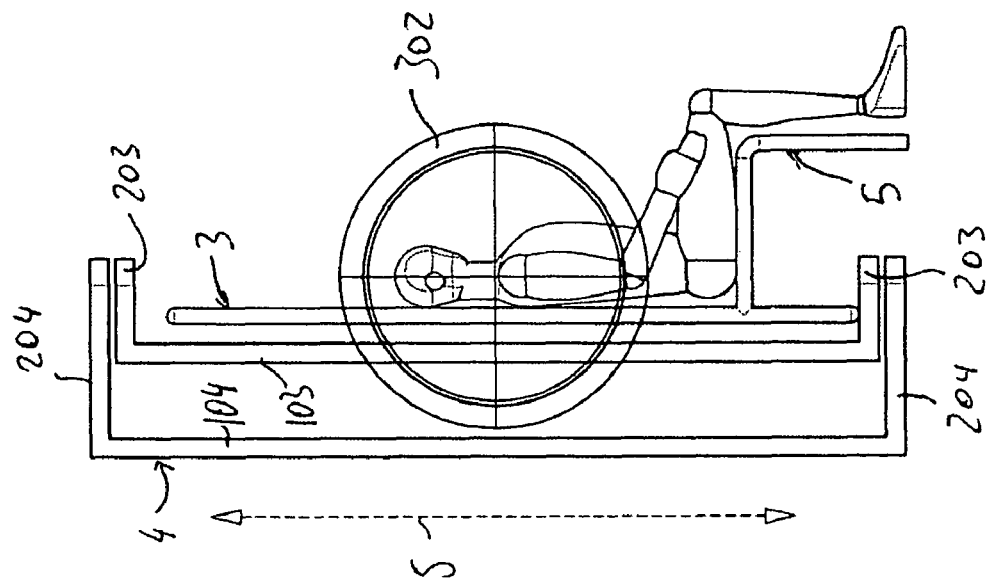
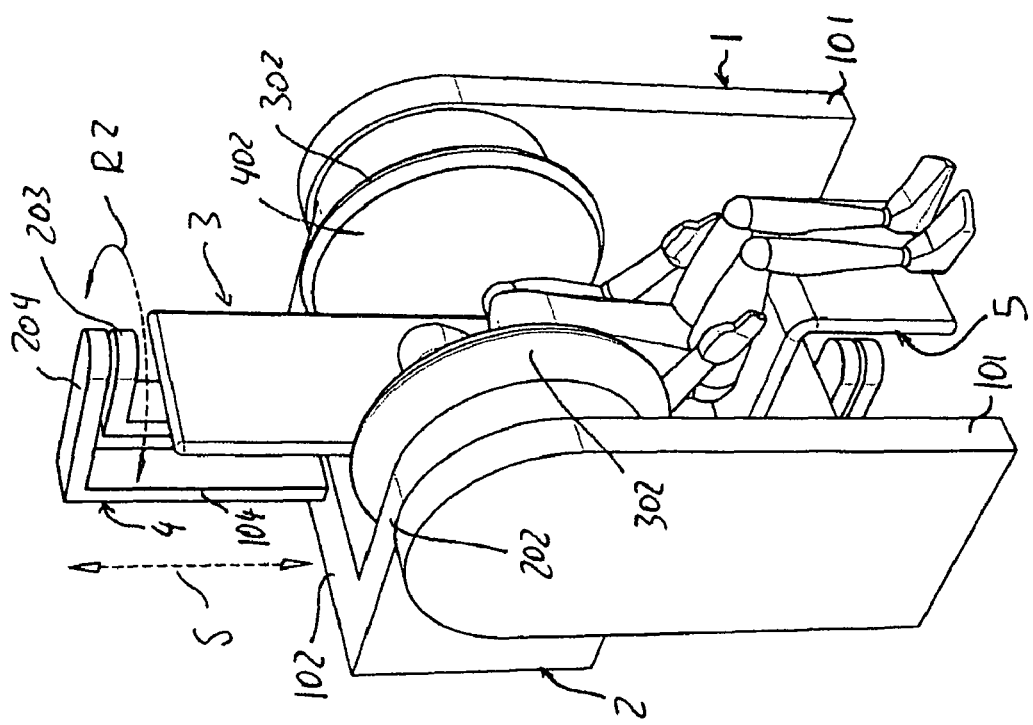

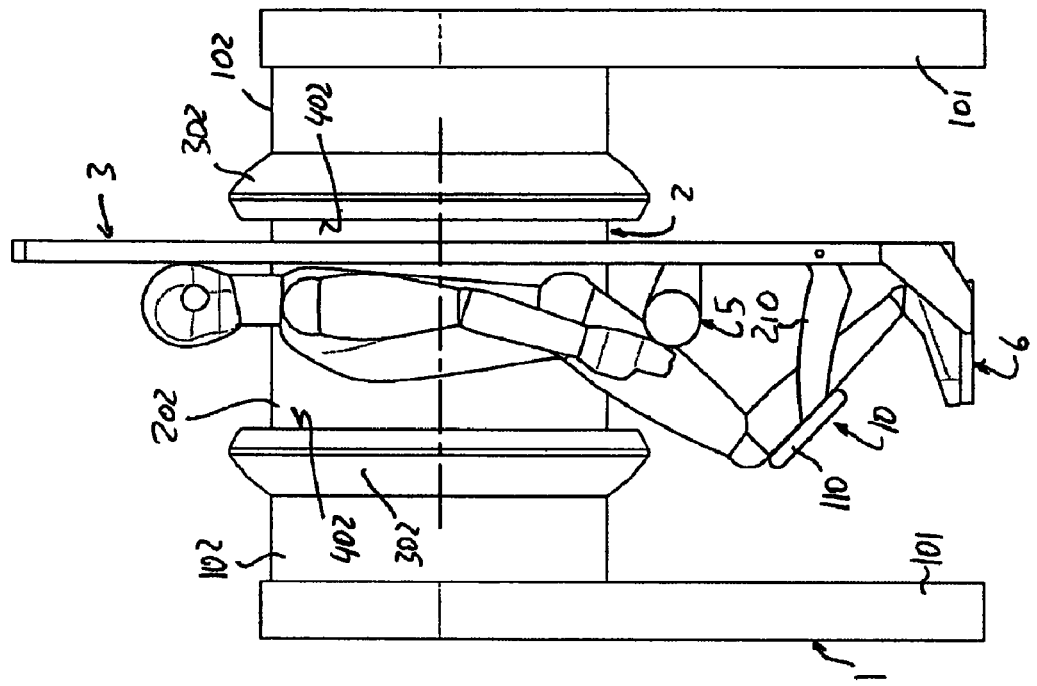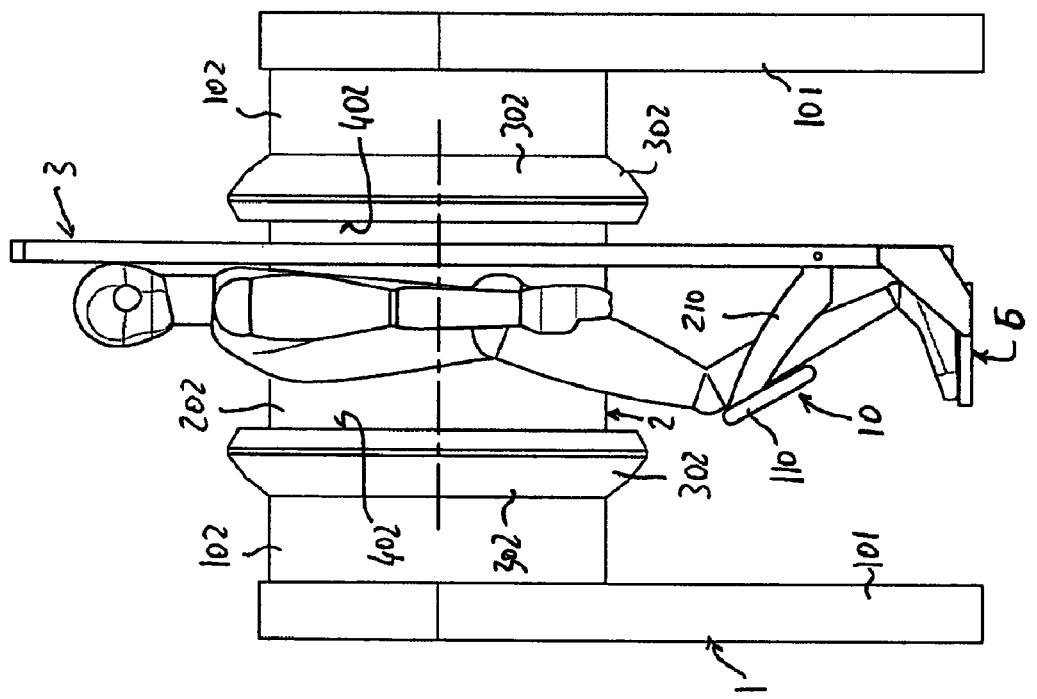

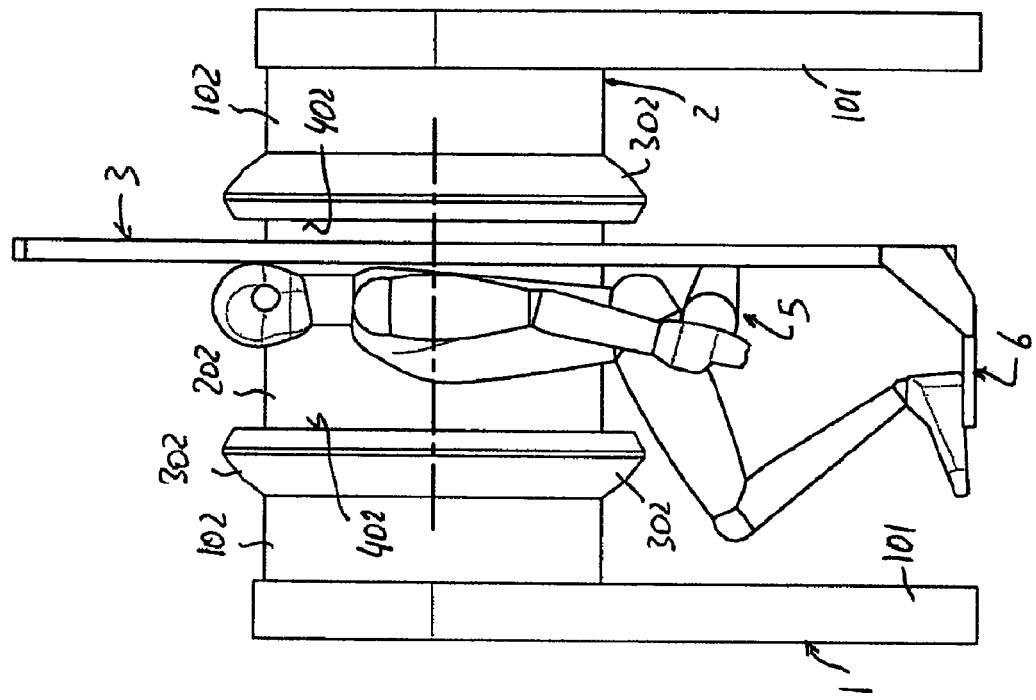
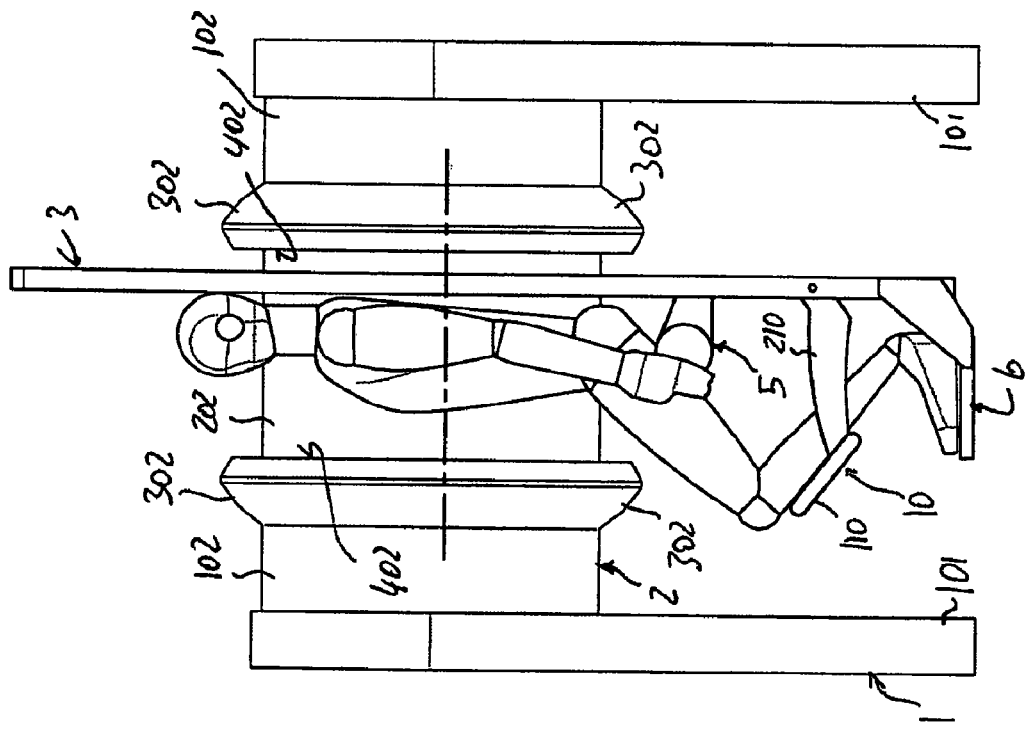
Fig. 12
Fig. 13

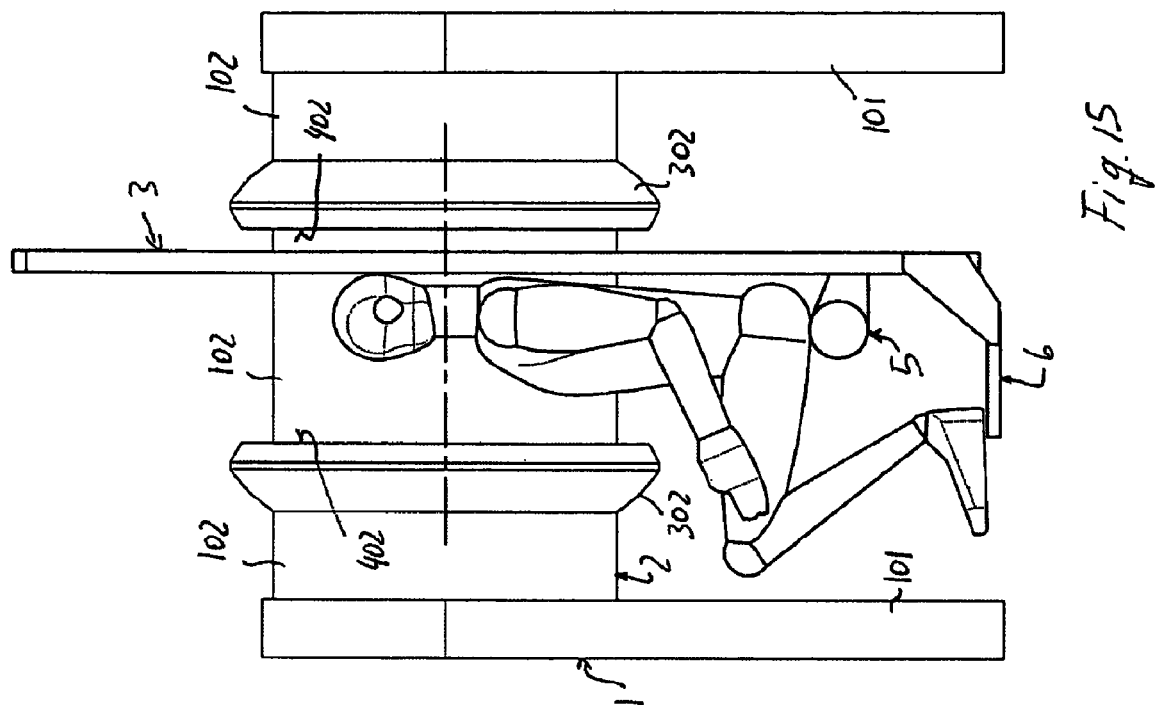
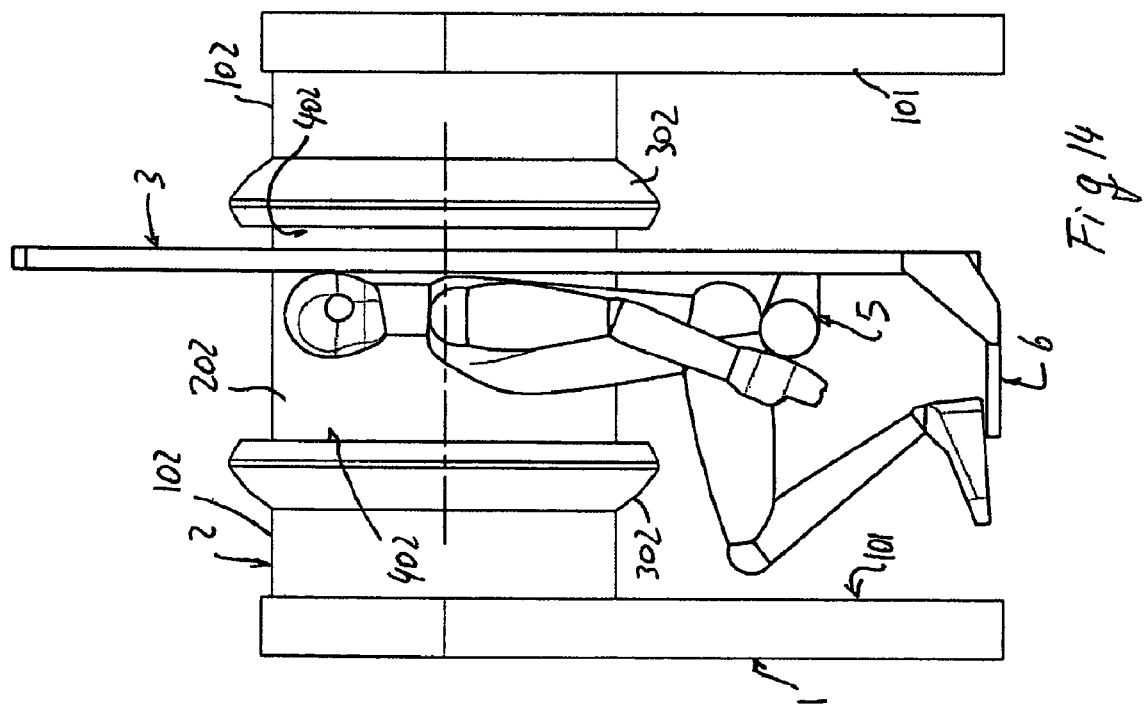

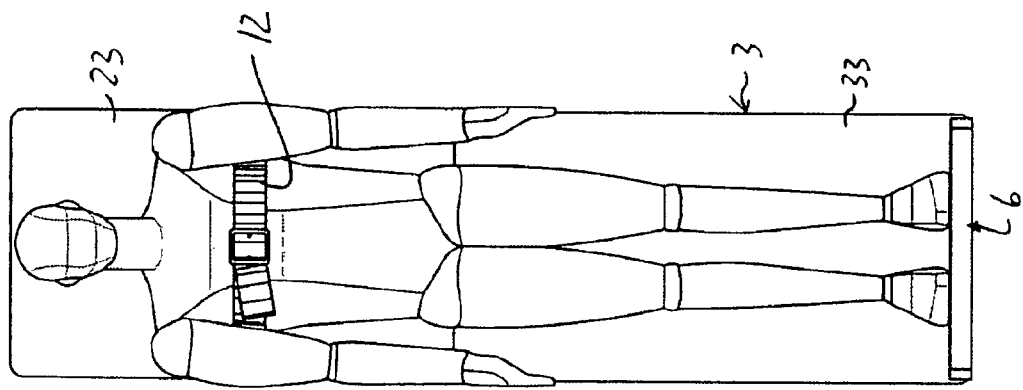
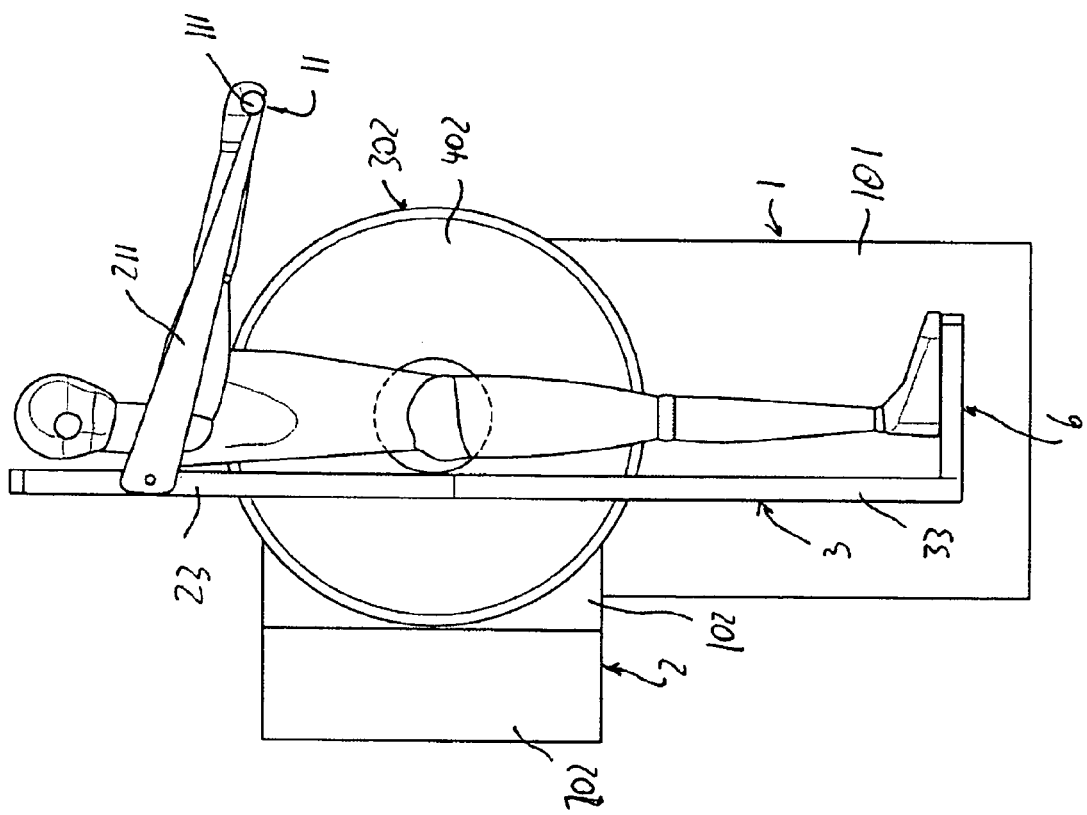

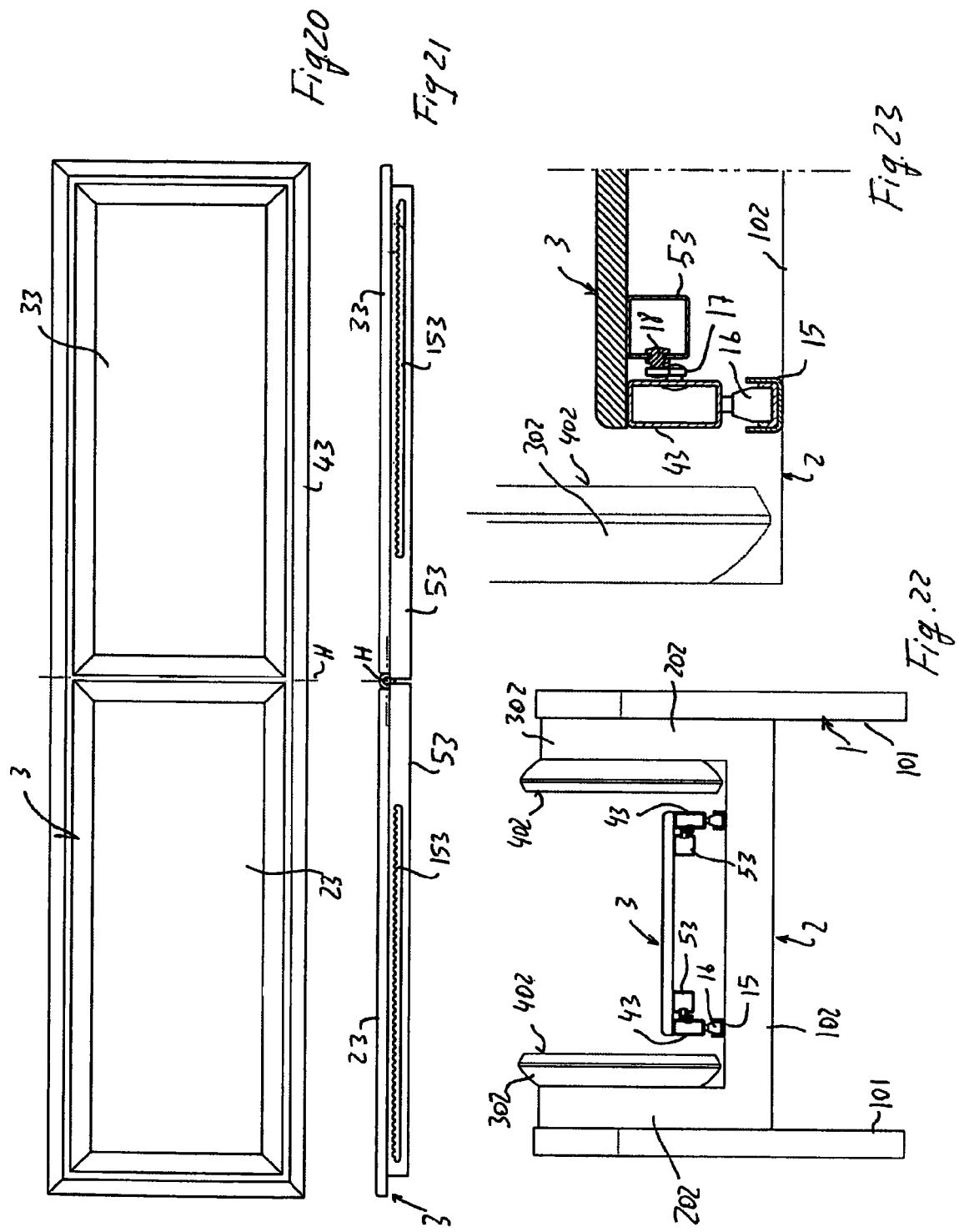

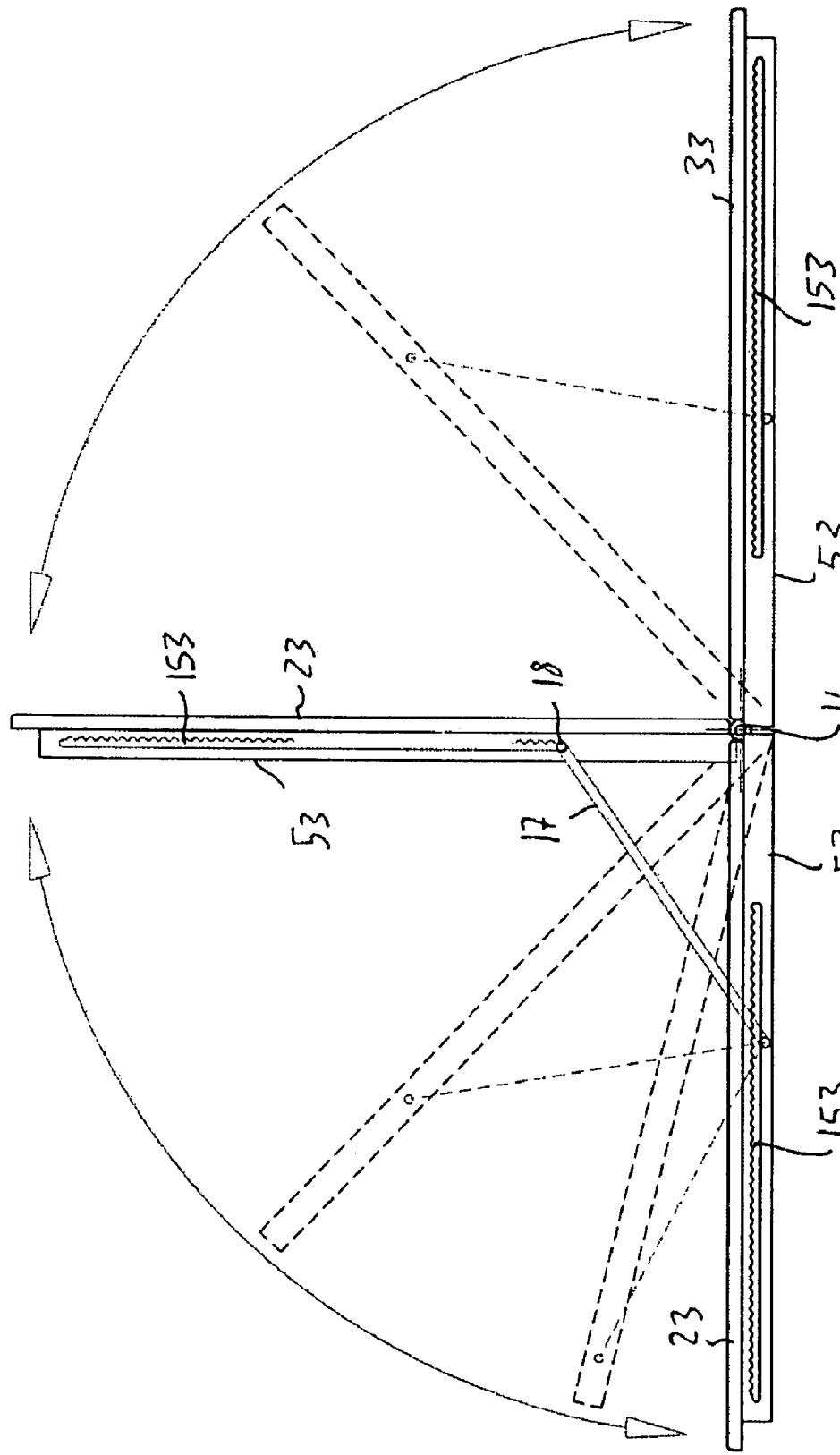

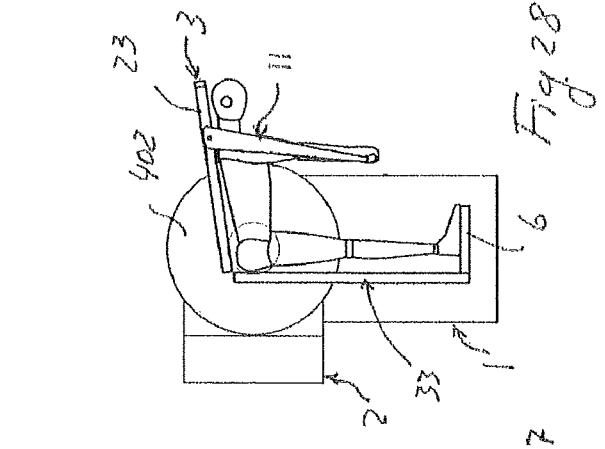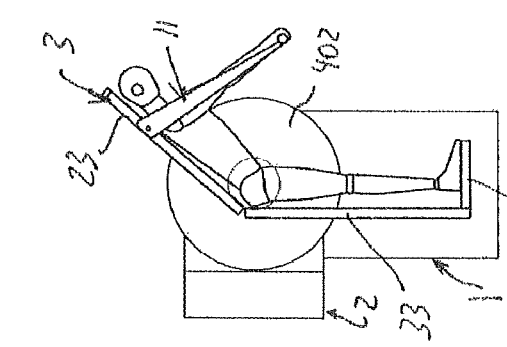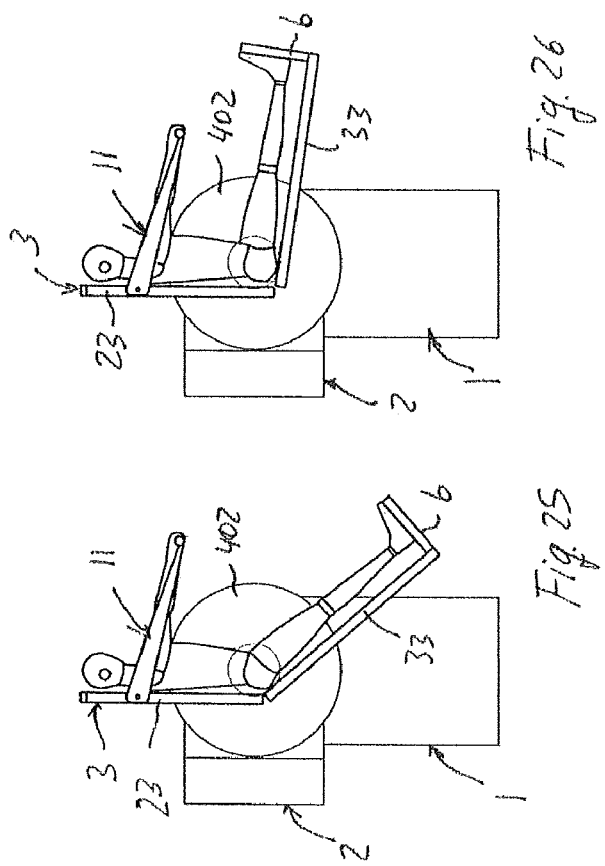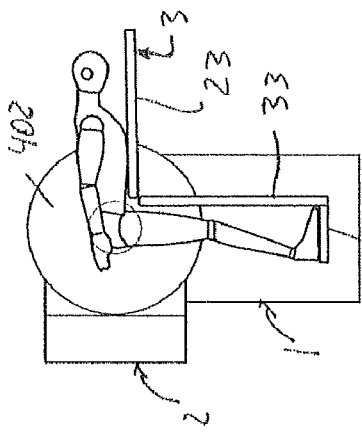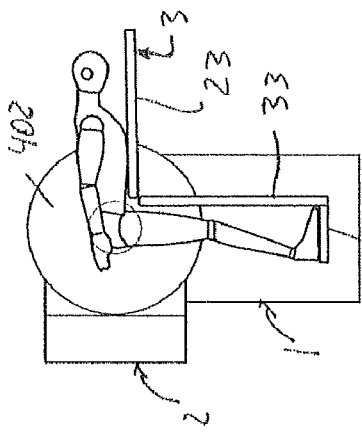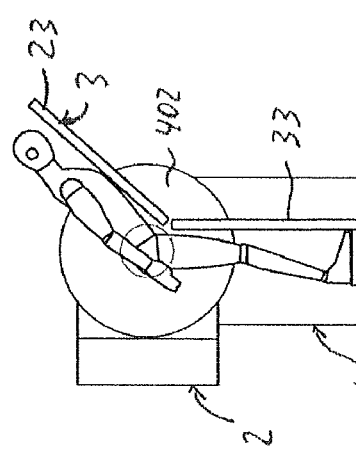

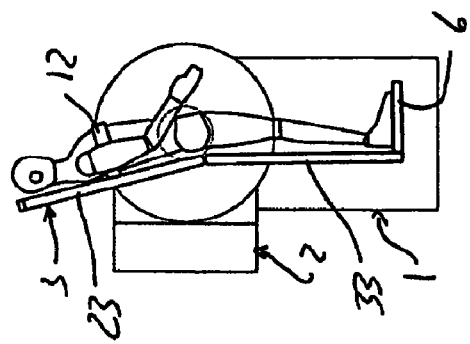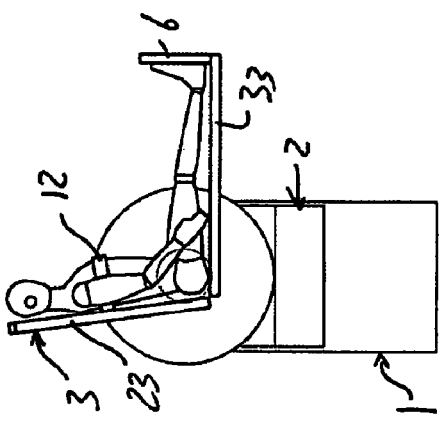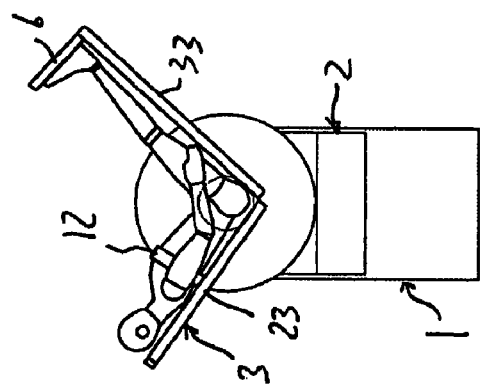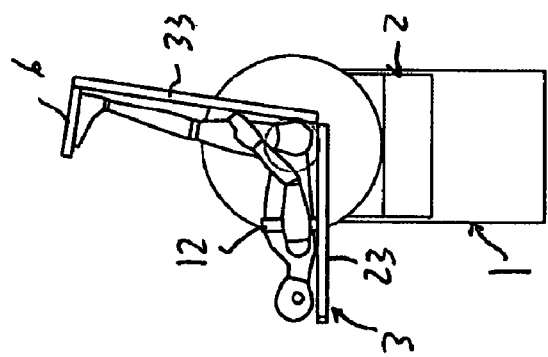

MAGNETIC RESONANCE IMAGING APPARATUS

BACKGROUND OF THE APPLICATION

1. Field of the Invention

The invention relates to a magnetic resonance imaging apparatus, and particularly to a multipurpose dedicated imaging apparatus having improved features for imaging the region of the vertebral column under different load conditions.

2. Description of the Related Art

Imaging the vertebral column may require the possibility of bringing the patient in an upright position in order to have the vertebral column loaded by the weight of the patient. In the normal laying down position of the patient on a bed or table having an horizontal orientation, the vertebral column will be in an unloaded and ideal condition. Thus, most pathologies may not arise clearly and the examination will lead to unclear results or to negative results despite the fact that the patient is showing typical symptoms of a disease of the vertebral column.

Most spinal disease can be best evaluated by imaging the anatomic region with the patient having different postures particularly a posture in which the patient is bent as a sitting position or a forward leaned position. Furthermore for best imaging the anatomic region it might be advantageous to be able to take images of the spine according to differently oriented imaging planes corresponding to different orientation of the static field direction parallel to a front/rear section plane of the patient or to a lateral section plane of the patient. The possibility of assuming different positions within the poles of a MRI apparatus are also important when interventions has to be carried out during the imaging process. In this case the patient position relative to the magnetic structure is important for leaving enough free space for the medical personal to reach the anatomic region where the intervention has to be carried out.

Allowing that the patient can assume different postures is also very important, since in case of pathological conditions the patient cannot take some postures for a long time without suffering pain. Since imaging sequences need normally a long time to be carried out in a manner of furnishing images of the anatomic region which are useful for diagnostic purposes, the patient must be able to maintain a certain position without making any movement for such a long time, which is impossible or at least highly disagreeable when the said position is associated with a posture of the patient at which the patient experiences pain.

Furthermore it is also relevant to ensure the possibility of carrying out a range as wide as possible of imaging different anatomical districts with one and the same imaging apparatus.

Actually known magnetic resonance imaging apparati use so called total body scanners which magnetic structure houses the entire body or a considerable part of it inside the patient examining space defined by the magnetic structure.

U.S. Pat. Nos. 6,414,490 and U.S. Pat. No. 6,504,371 disclose magnetic resonance imaging apparatus of the above mentioned kind. The magnetic structure is designed to generate a horizontal magnetic field. The patient is brought inside the examining space by means of a patient positioning device which is a bed or table mounted on a carriage, which bed or table can be further tilted around horizontal axis for giving different orientations to the bed or table with respect to the vertical direction. Furthermore, in order to focus the region of the patient to be imaged, the bed or table or carriage may be associated with an elevator which displaces the patient up and down relative to the examining space between the poles of the magnetic structure.

The patient positioning device is also relative expensive due to the fact that the tiltable or swingable bed or table and the elevator for displacing the patient relative to the imaging space in the magnetic structure are mounted on a carriage.

On the other hand, even if the anatomic region of the vertebral column is a very large one, usually examination through imaging is carried out for only a certain specific part of the vertebral column.

U.S. Pat. No. 5,689,190 and U.S. Pat. No. 5,666,056 disclose an MRI apparatus in which the poles of the magnetic structure have opposite surfaces delimiting an imaging space which surfaces are parallel to one another and which surfaces are oriented at an angle relative to a bed or table where the patient is laying. The bed or the table can be displaced along two perpendicular axes which are parallel to the plane defined by them.

Also in this case the magnetic structure is very big and there is a need of different patient supporting devices in order of allowing the patient to take different positions such as a laying position and a sitting position.

U.S. Pat. No. 6,011,396 shows a displaceable MRI apparatus which is mounted on a carriage and which has a magnetic structure with two opposite poles having surfaces limiting an image volume which are parallel one with respect to the other and oriented vertically. The two poles are tiltable together along the said vertical planes and have a relative distance which allow to drive between the two poles different devices for supporting a patient such as a table, a bed or a seat.

This MRI apparatus is indeed very small. Nevertheless for imaging the patient in different positions, particularly in a upright position, an elevator for the relative heavy magnetic structure is needed which on the other hand will have a correspondingly strong construction. Since the patient supporting and/or retaining device is a normal device such as a bed a seat or the like, no particular device is provided which is mechanically linked to the magnetic structure in order of having a precise and controlled relative positioning of the patient and of the magnetic structure.

U.S. Pat. No. 5,423,315 discloses an MRI apparatus having a thin annular magnetic structure which is mounted on a supporting frame allowing the said annular magnetic structure to be tilted around a first diametric axis and a second axis coinciding with the central axis of the annular magnetic structure. Furthermore the annular structure can be displaced along a vertical axis.

In the case of this device, the annular magnetic structure must have a very large diameter in order to allow access of the medical personal to the anatomical region of patient which is subjected to imaging.

Most of the actual devices are very big, heavy, and expensive. Big and heavy magnetic structures have problems of installation, since the room where the imaging apparatus has to be installed must necessarily have a floor which can support the weight of the imaging apparatus. Furthermore, the room must be sufficiently big to permit installation.

OBJECTS AND SUMMARY

An object of the present invention is to provide for a magnetic resonance imaging apparatus which has a smaller magnetic structure than the conventional so called total body apparatus and which allows nevertheless imaging of the vertebral column under various conditions, this means in various positions of the patient relative to the magnetic structure of the MRI apparatus and with the patient taking different postures.

A further aim is to provide for such a magnetic imaging apparatus which has simpler and less expensive means for positioning the patient in the examination space of the magnetic structure.

A further object of the present invention is to provide for a magnetic resonance imaging apparatus which can be used also for examinations of other anatomic regions of the body of the patient, by allowing in a simple way to displace the patient relative to the examination space in the magnetic structure in order to bring the desired anatomic region or a certain limited region thereof in the examination space.

Still another object of the present invention is to allow a free access of medical personal to the anatomical region of the patient being imaged in most of the postures of the patient allowing to carry out interventions on the patient during or after and before acquisition of the images.

A further object of the present invention is to allow to the patient to take painless or less painful postures during imaging maintaining a control and a sufficient precision of the relative position of the patient and the magnetic structure.

One embodiment of the present invention includes a magnetic resonance imaging apparatus comprising a magnet having two opposite and spaced apart poles and a column or wall transverse to the poles and connecting the poles;

the poles defining two opposite walls delimiting a patient-imaging space, the two opposite walls extending along substantially parallel planes which are substantially parallel to a vertical plane;

and a patient positioning table which is slidably connected to a supporting frame between the two poles; the table being positioned with its longitudinal axis substantially parallel to the said two opposite parallel walls of the poles and the said table being oriented with its transverse axis substantially perpendicular to at least one of the said two opposite walls;

the table being slidable with respect to the magnet in a direction parallel to a longitudinal axis of the table;

a drive for displacing the table relative to the magnet along the longitudinal axis; a lock for locking the table in a selected position relative to the magnet;

the magnetic structure and the table supporting frame with the table being supported rotatably along a central horizontal axis substantially perpendicular to at least one or both of the two opposite walls of the poles;

a drive being provided for rotating together the magnetic structure, the table supporting frame and the table and about the said axis;

the magnetic structure, the table supporting frame and the table being rotatable from a position in which the table is substantially horizontal to a position in which the table is substantially vertical, and vice versa.

Preferably only the poles of the magnetic structure are supported rotatable together with the table supporting frame around the same axis transverse to the table.

In a possible variant only the table supporting frame with the table are rotatable around the transverse axis.

In a further embodiment the table supporting frame with the table, and the magnetic structure may be rotatable independently one from the other around the same or a different axis of rotation an independent drive and independent removable locking means of the rotation being provided for the table supporting frame and the magnetic structure.

The term substantially parallel has the meaning within the present application that the table or bed may be aligned exactly along the axis of symmetry between the facing surfaces of the opposite poles or it may be slightly misaligned or laterally translated or laterally inclined in such a measure as allowed by the distance of the facing pole surfaces and/or in such a way that the table or the bed does not come into contact with the poles of the magnetic structure.

The term substantially horizontal and substantially vertical has the meaning within the present application that the table or bed can be oriented in the exact vertical or horizontal position and also in a position which is slightly inclined in one or both directions relative to the exact vertical or horizontal position of the table or of the bed.

A similar meaning of the term substantially has to be applied for the terms substantially perpendicular or substantially coinciding.

In a particular embodiment, the axis of rotation of the table supporting frame and of the poles substantially coincides with the central axis of the poles.

The rotation may be continuous or stepwise and removable locking means may be provided which allows to lock the table and/or the table supporting frame and/or the magnetic structure in an angular position which is intermediate between the horizontal position and the vertical position and/or in an angular position which is beyond the horizontal position or over the vertical position.

A further improvement consists in the fact that the apparatus is provided further with a magnetic structure supporting basement having two lateral walls to which the magnetic structure is rotatably connected at the rotation axis of the poles; the poles being provided at the two opposite free ends of a U-shaped yoke the central branch of it being oriented horizontally and substantially parallel to the rotation axis, which central branch of the U-shaped magnetic structure supports the table supporting frame in a slidable way along a longitudinal direction of the table; the two opposite lateral branches of the U-shaped yoke supports at their ends the poles and the magnetic structure is supported rotatably around the common axis of rotation by means of the poles being hinged to the lateral walls of the supporting basement of the magnetic structure.

According to a further improvement of the said embodiment, the table is further supported on the supporting frame in a rotatable manner around its central longitudinal axis; a drive being provided for rotating the table relative to the magnet along the central longitudinal axis; a removable lock for locking the table in a selected position relative to the magnet being also provided.

From the constructive point of view the table supporting frame is formed by an elongated element slidably engaged with the central branch of the U-shaped magnetic yoke; the table supporting frame has also an U shaped form with the central branch extending in the longitudinal direction of the table and with the angled end branches projecting from the central branch in a measure which is greater than the half width of the table while both transverse ends of the table are rotatably secured around a common axis of rotation at the free ends of the end branches of the table supporting frame.

According to a further improvement the table is secured to a second table supporting frame which is also U-shaped; the second supporting frame having an elongated central branch directly secured to the rear side of the table and which end branches project forward at both transverse ends of the table; the said end branches of the said second table supporting frame having a length which is shorter relative to the length of the end branches of the first table supporting frame and being rotatably secured with their ends to the ends of the end branches of the said first table supporting frame.

Still according to a further improvement which can be provided in combination with both or at least one of the preceding combinations of features, the table has a table plate and is further provided with at least one seat plate which is swingable from a position parallel to the said table plate into a position perpendicular to the said table plate and in which swung position part of the table plate forms a back of a seat.

A further improvement consist in the fact that the said seat plate is formed by a part of the table plate the table plate being formed by at least two parts hinged together at least one of which forms the swingable seat plate.

According to a further feature which can be provided separately or in combination with the aforementioned features, the table plate is formed at least by two parts which are hinged together along a transversal axis of the plate at least one of the two parts of the table being swingable in a position perpendicular to the other part so that the table has an angled shape, particularly a vertical part and an horizontal part which works as a support for the patient either in a bend forward or in bend backward position depending whether the patient is laying on the able with its back or with its frontal side.

The footrest and or the seat plate may be supported on the table or on the table supporting frame by means of a guide allowing to the footrest ad/or to the seat to slide along the table or along the table supporting frame in both direction parallel to the longitudinal axis of the table and/or of the table supporting frame.

The table and or the table supporting frame may be further provided with means for retaining the patient against the table in different positions thereof.

According to one embodiment the table or the frame may be provided with one or more removable fastening belts of the patient against the table.

A further embodiment of the said retaining means which can be provided alternatively or in combination to the above mentioned belts could be formed by means for supporting the patient cooperating with the armpits of the patient.

Another alternative which can be provided alone or in combination of the above mentioned retaining means provides a knee retaining support against which the patient, can push the knees and/or the leg in order to exercise a force helping to maintain a position adherent to the table or the bed.

These knee retaining means may be slidable along the table or the table supporting frame in the longitudinal direction thereof and can also be displaced angularly.

In order to obtain these various solutions may be applied as for example supporting the knee retaining means on a slide mounted on guides oriented in the longitudinal direction of the table or of the table supporting frame. The knee retaining means may be secured to the slide by means of rotatable supports such as brackets hinged on the guide in a rotatable manner around a common axis which is substantially transversal to the table or to the table supporting frame.

The footrest and/or the seat and/or the belts and/or the retaining means cooperating with the armpit can also be mounted on slides associated to guides on the table or on the table supporting frame and can also be secured to the slide by means of hinges allowing at least an angular displacement along at least one axis transversal to the table and/or to the table supporting frame.

As it will appear more clearly from the following detailed description of a preferred embodiment, the above slidable and angularly displaceable footrest, knee retaining means, seat, securing belts and or the slidable and angularly displaceable retaining means cooperating with the armpit allows to the patient to take a very wide range of different postures during examination, which may correspond to different kinds of mechanical stress or load of the relevant target in the anatomical district to be imaged and this is particularly relevant for examination of spinal pathologies but not limited to this kind of examination.

The above mentioned slidable and angularly displaceable footrest, knee retaining means, seat, securing belts and or the slidable and angularly displaceable retaining means cooperating with the armpit can be provided further with locking means for blocking the footrest, knee retaining means, seat, securing belts and or the slidable and angularly displaceable retaining means cooperating with the armpits in a chosen position relative to a sliding and or to an angular displacement.

Furthermore according to an improvement, the sliding and/or angular displacement of the footrest, knee retaining means, seat, securing belts and or the slidable and angularly displaceable retaining means cooperating with the table as well as the locking in position and unlocking of the footrest, knee retaining means, seat, securing belts and or the slidable and angularly displaceable retaining means cooperating with the armpits may be carried out manually or by means of motorized means such as electric motors and/or hydraulic motors or actuators.

The footrest, knee retaining means, seat, securing belts and or the slidable and angularly displaceable retaining means cooperating with the armpits may be mechanically or electromechanically or electrically interlinked relative to their sliding and or angular displacement in order to correlate different positions of at least two, or of at least a selected group or of all of the said footrest, knee retaining means, seat, securing belts and or the slidable and angularly displaceable retaining means cooperating with the armpits with each other according to one or more anatomically defined and compatible positions for the patient.

Other retaining means may be provided such as for examples handles or the like secured to the frame of the apparatus and/or to the table and/or to the table supporting frame and/or to the magnetic structure, which handles may be grasped by the patient and which handles may be also displaceable in order to take different orientations relative to the position of the table and/or of the table supporting frame.

The present invention provides furthermore of a method for magnetic resonance imaging with a magnetic structure having two opposite poles spaced apart one from the other and oriented substantially parallel to a vertical plane and defining a patient imaging space; and a table for a patient secured to a table supporting frame in a slidable way in a substantially longitudinal direction of the table relative to the magnetic structure and between the two poles of the magnetic structure, the table being oriented at least substantially perpendicular to at least one of the poles, the table having a footrest at one end thereof, at least the poles of the magnetic structure and the table supporting frame and the table and/or the magnetic structure being rotatable together around an axis which is transverse to a longitudinal axis of the table and parallel to the table.

The method comprises:
rotating at least the poles of the magnetic structure and the supporting frame with the table to a patient positioning position in which the table is substantially horizontal;
sliding the table to an end position, in which a part of the table is outside the magnetic structure;
arranging the patient on the table in a laying down position;
sliding the table along its longitudinal axis relative to the magnetic structure until the magnetic structure is correctly centered with a part of the patient's body to be examined;

locking the table or the table supporting frame with the table relative to the magnetic structure in a position in which the table is horizontal;
carrying out an imaging procedure;
unlocking the table or the table supporting frame with the table relative to the magnetic structure; and
sliding the table to one position in which a part of the table is outside the magnetic structure and letting the patient step down from the table.

The patient may be arranged on the table in a prone or in a supine position.

Another embodiment of the present invention includes a method for magnetic resonance imaging with at least a magnetic structure having two opposite poles spaced apart one from the other and oriented substantially parallel to a vertical plane and defining a patient imaging space; and a table for a patient secured to a table supporting frame in a slidable way in a substantially longitudinal direction of the table relative to the magnetic structure and between the two poles of the magnetic structure, the table being oriented at least substantially perpendicular to the poles, the table having a footrest at one end thereof, at least the poles of the magnetic structure and the table supporting frame and the table being rotatable together around an axis which is substantially transverse to a longitudinal axis of the table and substantially parallel to the table;

The method comprises:
rotating at least the poles and the supporting frame with the table to a patient positioning position in which the table is substantially horizontal;
sliding the table to an end position, in which a part of the table is outside the magnetic structure;
arranging the patient on the table in a laying down supine or prone position;
sliding the table and/or the table supporting frame along its longitudinal axis relative to the magnetic structure until the magnetic structure is correctly centered with a part of the patient's body to be examined;
locking the table and/or the table supporting frame in the said position at which the magnetic structure is centered with the part to be imaged;
rotating at least the poles and the table supporting frame together with the table to a position in which the table is oriented in an intermediate angular position between the horizontal position and the vertical position or in which the table is oriented substantially vertical;
locking at least the poles and the table and/or the table supporting frame with the table in the said intermediate angular position or in the said substantially vertical position;
carrying out an imaging procedure;
unlocking the magnetic poles and/or the table and/or the table supporting frame with the table relative to a rotation;
rotating at least the poles and/or the table and/or the table supporting frame in a position in which the table is substantially horizontal;
unlocking the table and/or the table supporting frame with the table relative to at least the magnetic poles;
sliding the table to one position in which a part of the table is outside the magnetic structure and letting the patient step down from the table.

Carrying out the above method the patient may be positioned in a supine position on the table.

The above method may be carried out in combination with a patient which is positioned prone on the table.

Furthermore the above method can be also carried out with the patient either in the prone position or in the supine position by rotating at least the poles of the magnetic structure and the table and/or the table supporting frame with the table in an angular position over the vertical position, i.e., in an angular position in which the side on which the patient is laying is oriented with a component of the direction of orientation directed downwards, patient supporting and/or retaining means being provided for retaining the patient against the table surface in an anatomically compatible desired position.

In this case the patient supporting and/or retaining means can be for example a slidable and angularly displaceable footrest, knee retaining means, seat, securing belts and or a slidable and angularly displaceable retaining means cooperating with the armpits allowing to the patient to take a very wide range of different postures during examination, which may correspond to different kinds of mechanical stress or load of the relevant target in the anatomical district to be imaged and this is particularly relevant for examination of spinal pathologies but not limited to this kind of examination, these retaining means being of the kind of means requesting that the patient exercise an active retaining force or of the kind requesting no active participation of the patient.

As already disclosed above these means may be displaced manually or by means of motorized actuators and/or these means cooperate with locking and unlocking means relative to the sliding or to the angular displacement and these means may also be interlinked mechanically, electromechanically or electrically.

Thus the method as disclosed above may comprise the further steps of
positioning the patient supporting and/or retaining means according to a selected patient posture;
locking the said patient supporting and/or retaining means in the selected position and activating the patient supporting and/or retaining means for retaining the patient against the table before rotating at least the poles and the table supporting frame together with the table to from the substantially horizontal position to a position in which the table is oriented in an inclined position over the vertical position with the supporting surface of the table oriented with one component oriented downwards;
and unlocking the said patient supporting and/or retaining means in the selected position and deactivating the patient supporting and/or retaining means for putting the patient free after having rotated back at least the poles and the table supporting frame together with the table to from the substantially horizontal position to a position in which the table is oriented in an inclined position over the vertical position with the supporting surface of the table oriented with one component oriented downwards.

Another embodiment of the present invention includes a method for magnetic resonance imaging with a magnetic structure having two opposite poles spaced apart one from the other and oriented substantially parallel to a vertical plane and defining a patient imaging space; and a table for a patient secured to a table supporting frame in a slidable way in a substantially longitudinal direction of the table relative to the magnetic structure and between the two poles of the magnetic structure, the table being oriented at least substantially perpendicular to the poles, the table having a footrest at one end thereof, at least the poles of the magnetic structure and the table supporting frame and the table being rotatable together around an axis which is substantially transverse to a longitudinal axis of the table and substantially parallel to the table; the table being rotatable around its longitudinal axis relative to the supporting frame and to the magnetic structure.

The method comprises:

rotating at least the poles and the supporting frame with the table to a patient positioning position in which the table is substantially horizontal;

sliding the table to an end position, in which a part of the table is outside the magnetic structure;

arranging the patient on the table in a laying down supine or prone position;

sliding the table and/or the table supporting frame along its longitudinal axis relative to the magnetic structure until the magnetic structure is correctly centered with a part of the patient's body to be examined;

locking the table and/or the table supporting frame in the said position at which the magnetic structure is centered with the part to be imaged;

rotating at least the poles and the table supporting frame together with the table to a position in which the table is oriented in an intermediate angular position between the horizontal position and the vertical position or in which the table is oriented substantially vertical;

locking at least the poles and the table and/or the table supporting frame with the table in the said intermediate angular position or in the said substantially vertical position;

rotating the table around its longitudinal axis in a position in which the table is parallel to the magnetic poles or at an angle to at least one of the magnetic poles;

locking the table relative to the table supporting frame and/or to the magnetic structure in the said angular position parallel or at an angle relative to at least one of the magnetic poles;

carrying out an imaging procedure;

unlocking the table relative to the table supporting frame and/or to the magnetic structure;

rotating the table around its longitudinal axis back in a position in which the table is perpendicular to at least one of the magnetic the poles;

unlocking the magnetic poles and/or the table and/or the table supporting frame with the table relative to a rotation;

rotating at least the poles and/or the table and/or the table supporting frame in a position in which the table is substantially horizontal;

unlocking the table and/or the table supporting frame with the table relative to at least the magnetic poles;

sliding the table to one position in which a part of the table is outside the magnetic structure and letting the patient step down from the table.

Similarly to the preceding embodiment, also inn the case of the above embodiment there might be provided patient supporting and/or retaining means which can help in helping the patient to take different postures during examination.

A further embodiment of the present invention includes a method for magnetic resonance imaging with a magnetic structure having two opposite poles spaced apart one from the other and oriented substantially parallel to a vertical plane and defining a patient imaging space; and a table for a patient secured to a table supporting frame in a slidable way in a substantially longitudinal direction of the table relative to the magnetic structure and between the two poles of the magnetic structure, the table being oriented at least substantially perpendicular to the poles, the table having a footrest at one end thereof, at least the poles of the magnetic structure and the table supporting frame and the table being rotatable together around an axis which is substantially transverse to a longitudinal axis of the table and substantially parallel to the table; the method comprises:

rotating at least the poles and the supporting frame with the table to a patient positioning position in which the table is substantially horizontal;

sliding the table to an end position, in which a part of the table is outside the magnetic structure;

arranging the patient on the table in a laying down supine or prone position;

sliding the table and/or the table supporting frame along its longitudinal axis relative to the magnetic structure until the magnetic structure is correctly centered with a part of the patient's body to be examined;

locking the table and/or the table supporting frame in the said position at which the magnetic structure is centered with the part to be imaged;

rotating at least the poles and the table supporting frame together with the table to a position in which the table is oriented in an intermediate angular position between the horizontal position and the vertical position or in which the table is oriented substantially vertical;

locking at least the poles and the table and/or the table supporting frame with the table in the said intermediate angular position or in the said substantially vertical position;

carrying out an imaging procedure;

unlocking the magnetic poles and/or the table and/or the table supporting frame with the table relative to a rotation;

rotating at least the poles and/or the table and/or the table supporting frame in a position in which the table is substantially horizontal;

unlocking the table and/or the table supporting frame with the table relative to at least the magnetic poles;

sliding the table to one position in which a part of the table is outside the magnetic structure and letting the patient step down from the table.

Similarly to the preceding embodiment, also in the case of the above embodiment there might be provided patient supporting and/or retaining means which can help in helping the patient to take different postures during examination.

Another embodiment of the present invention includes a method for magnetic resonance imaging with a magnetic structure having two opposite poles spaced apart one from the other and oriented substantially parallel to a vertical plane and defining a patient imaging space; and a table for a patient secured to a table supporting frame which table or which table supporting frame with the table are slidable in a longitudinal direction of the table relative to the magnetic structure and between the two poles of the magnetic structure, the table being oriented at least substantially perpendicular to at least one of the poles; the table having a footrest at one end thereof; at least the poles of the magnetic structure and the and the table and/or the table supporting frame with the table being rotatable together around an axis which is transverse to a longitudinal axis of the table and substantially parallel to the table; the table being further rotatable around its longitudinal axis relative to the supporting frame and to the magnet; the table being formed by a first and a second part which are hinged together in such a way that the first part of the table can be displaced angularly in a position at an angle or substantially perpendicular with respect to the second part of the table along a substantially transverse axis of the table or of the table supporting frame, locking means being provided for locking the first and second part of the table in the angled position relative to the second part of the table;

The method comprises:

rotating at least the poles and the table and/or the table supporting frame with the table to a patient positioning position in which the table is substantially horizontal;

sliding the table to an end position, in which a part of the table is outside the magnetic structure;

arranging the patient on the table in a laying prone position;

sliding the table along its longitudinal axis relative to the magnetic structure until the magnetic structure is correctly centred with a part of the patient's body to be examined;

locking the table in the said position relative to a sliding;

rotating the at least the poles and the table and/or the supporting frame together with the table to a position in which the table is in an intermediate angular position between the said substantially horizontal and the said substantially vertical position or in the said substantially vertical position;

locking at least the poles and the table and/or the table supporting frame with the table in the said intermediate angular position or in the said substantially vertical position;

swinging rearward the first part of the table which forms the upper part of the vertically oriented table in a position in which the said first part of the table is at an angle or in an horizontal position in the direction of the back of the table;

locking the said first part of the table in the said swung back position relative to the substantially vertical oriented second part of the table carrying out an imaging procedure;

unlocking the said first part of the table in the said swung back position relative to the second part of the table;

swinging forward the first part of the table back in the position in which it is aligned with the second part of the table;

unlocking at least the poles and the table and/or the table supporting frame with the table in the said intermediate angular position or in the said substantially vertical position;

rotating at least the table and the supporting frame in a position in which the table is substantially horizontal;

unlocking the table in the said position relative to a sliding;

sliding the table to one position in which a part of the table is outside the magnetic structure and letting the patient step down from the table.

As an alternative the above method can be carried out with the patient laying in a supine position on the table, patient supporting and/or retaining means being provided for maintaining the patient in a position against the table when the two parts of the table are swung at an angle one with respect to the other.

The patient supporting and/or retaining means can be of any kind and particularly of the kind already disclosed in combination with the above mentioned embodiments.

Thus according to the above additional features the invention provides for a method for magnetic resonance imaging with a magnetic structure having two opposite poles spaced apart one from the other and oriented substantially parallel to a vertical plane and defining a patient imaging space; and a table for a patient secured to a table supporting frame which table or which table supporting frame with the table are slidable in a longitudinal direction of the table relative to the magnetic structure and between the two poles of the magnetic structure, the table being oriented at least substantially perpendicular to at least one of the poles; the table having a footrest at one end thereof; at least the poles of the magnetic structure and the table and/or the table supporting frame with the table being rotatable together around an axis which is transverse to a longitudinal axis of the table and substantially parallel to the table; the table being further rotatable around its longitudinal axis relative to the supporting frame and to the magnet; the table being formed by a first and a second part which are hinged together in such a way that at least one or both of the said two parts of the table can be displaced angularly in a position at an angle or substantially perpendicular with respect to the other part of the table along a substantially transverse axis of the table or of the table supporting frame, locking means being provided for locking at least one or both of the first and second part of the table in the angled position relative to the other part of the table; further comprising patient supporting and/or retaining means which can be activated and deactivated and which are displaceable either by sliding and or by an angular motion with respect to the table and/or to the table supporting frame;

The method comprises:

rotating at least the poles and the table and/or the table supporting frame with the table to a patient positioning position in which the table is substantially horizontal;

sliding the table to an end position, in which a part of the table is outside the magnetic structure;

arranging the patient on the table in a laying supine or prone position;

positioning the patient supporting and/or retaining means according to a selected posture desired for the patient during examination;

activating and locking the patient supporting and/or retaining means;

sliding the table along its longitudinal axis relative to the magnetic structure until the magnetic structure is correctly centered with a part of the patient's body to be examined;

locking the table in the said position relative to a sliding;

rotating at least the poles and the table and/or the supporting frame together with the table to a position in which the table is in an intermediate position between the substantially horizontal and the substantially vertical position or in which the table is substantially vertical;

locking at least the poles and the table and/or the table supporting frame with the table in the said intermediate angular position or in the said substantially vertical position;

depending on whether the patient was laid supine or prone on the table, swinging backward or rearward at least the first part or at least the second part or both the first and second part of the table which form the upper or lower part of table in a position in which the said first and second parts of the table are at an angle one with respect to the other;

locking the said two parts of the table in the said angled relative position;

carrying out an imaging procedure;

unlocking the said two parts of the table in the said angled relative position, swinging back at least the first part or at least the second part or both the first and second part of the table which form the upper or lower part of table in a position in which the said first and second parts of the table are again aligned one with respect to the other;

unlocking at least the poles and the table and/or the table supporting frame with the table in the said intermediate angular position or in the said substantially vertical position;

rotating at least the table and the supporting frame in a position in which the table is substantially horizontal;

unlocking the table in the said position relative to a sliding sliding the table to one position in which a part of the table is outside the magnetic structure and letting the patient step down from the table.

The above mentioned methods can be very useful when further to a simple examination of the patient also an intervention has to be carried out. In this case the intervention must normally be carried out in a relaxed and unstressed condition of the patient at least relative to the anatomical district where the intervention has to be carried out.

Thus depending on the fact whether the imaging has to be carried out during intervention or at a different time after having carried out the step of rotating back the table in the substantially horizontal position, instead of sliding the table or the table supporting frame with the table together with at least the poles of the magnetic structure the table and/or the table supporting frame with the table might be retained in the position at which the region under examination is centered relative to the imaging zone defined by the poles of the magnetic structure and the intervention is carried out. In this case imaging can be carried out during the intervention.

Alternatively the table or the table supporting frame with the table can be displaced by sliding along their longitudinal direction in a position relative to the poles of the magnetic structure at which the region being imaged and coinciding with the region where the intervention has to be carried out is offset in a position in which the region imaged and where the intervention has to be carried out is at a vicinity of the border of the poles of the magnetic structure either still in the volume between the poles or outside the volume between the poles so that the region where the intervention has to be carried out can be better reached.

In this case if during intervention a control image has to be carried out the intervention can be stopped at an intermediate stage and the table or the table supporting frame with the table can be brought again in the position in which the region of intervention coincides with the imaging volume between the poles of the magnetic structure.

Still another embodiment of the present invention includes a method for carrying out magnetic resonance imaging with a magnetic structure having two opposite poles spaced apart one from the other and oriented substantially parallel to a vertical plane and defining a patient imaging space; and a table for a patient mounted on a supporting frame in a slidable way in a longitudinal direction of the table relative to the magnetic structure and between the two poles of the magnetic structure, the table being oriented substantially perpendicular to the poles; at least the poles of the magnetic structure and the supporting frame and the table being rotatable together around an axis which is transverse to the longitudinal axis of the table and parallel to the table.

The method comprises:
rotating at least the poles and the supporting frame together with the table in a position in which the table is not horizontal;
providing a seat plate secured at an angle to the table;
sitting the patient down on the seat plate;
carrying out the imaging procedure; and
letting the patient step out of the magnetic structure.

Still another embodiment of the present invention includes a method for carrying out magnetic resonance imaging with a magnetic structure having two opposite poles spaced apart one from the other and oriented substantially parallel to a vertical plane and defining a patient imaging space; and a table for a patient mounted on a supporting frame in a slidable way in a longitudinal direction of the table relative to the magnetic structure and between the two poles of the magnetic structure, the table being oriented substantially perpendicular to the poles; at least the poles of the magnetic structure and the supporting frame and the table being rotatable together around an axis which is transverse to the longitudinal axis of the table and parallel to the table; the table being rotatable around its longitudinal axis relative to the supporting frame and to the magnet.

The method comprises:
rotating at least the poles and the supporting frame together with the table in a position in which the table is not horizontal;
providing a seat plate secured at an angle to the table;
sitting the patient down on the seat plate;
rotating the table around its longitudinal axis in a position in which the table is parallel to the magnetic poles or at an angle to the magnetic poles;
carrying out the imaging procedure;
rotating the table around its longitudinal axis back in a position in which the table is perpendicular to the poles, and letting the patient step out of the magnetic structure.

The MRI apparatus according to the present invention allows in a very rapid and simple manner and without the need of a very big and heavy construction to carry out the imaging on many kinds of anatomical regions of a patient, namely: Spine, shoulder, hand, wrist, elbow, hip, knee, ankle. The different postures and position of the patient allow to center the imaging volume on the different spine regions such as the cervical spine and the lumbar spine. Depending on the position and posture of the patient the MRI apparatus according to the invention allows to carry out imaging without stress or under stress of the following anatomical regions of the patients body: cervical and lumbar spine, knee, hip.

BRIEF DESCRIPTION OF THE DRAWINGS

FIGS. 6 and 7 are a lateral view and a perspective view of the imaging apparatus according to the present invention in which the position of the patient relative to the magnetic structure and the posture of the patient allow imaging in particular but not only of the cervical region of the spine under stress.

FIGS. 10, 11, 12 are lateral views of the apparatus according to the invention, in which the table is oriented in a vertical position and in which a footrest and knee supporting means are provided for allowing the patient to take different postures three of which are shown in the figures, while in FIGS. 11 and 12 also a seat is provided.

FIGS. 13, 14, 15 are three lateral views of the apparatus according to the invention in which a footrest and a seat are provided for allowing the patient to take different postures three of which are shown as an example, the footrest and/or the seat being slidable along the table in its longitudinal direction.

FIG. 16 shows the table and patient supporting and/or retaining means of the kind allowing the patient to actively push himself against the table by means of its arms.

FIG. 17 show the table and patient supporting and/or retaining means such as a belt securing the patient to the table.

FIG. 20 is a plane view on a table being formed by two parts swingable relative to one another and relative to a table supporting frame.

FIG. 21 is a lateral view of the table according to FIG. 20.

FIG. 22 is a view along an axis parallel to the longitudinal direction of the table showing the table, the table supporting frame and the magnetic structure together with the means for securing the table to the magnetic structure, particularly to the yoke of the magnetic structure.

FIG. 23 is a enlarged view of FIG. 22 in the region of the means for securing the table and the table supporting frame to the magnetic structure.

FIG. 24 is a lateral view of the table according to FIGS. 20 to 22 in which the two parts of the table are shown in different angular positions one relative to the other and relative to the table supporting frame.

FIGS. 25 to 34 shows some examples of different postures which can be taken by the patient with the apparatus according to the invention in combination with a table according to the previous FIGS. 20 to 24.

DETAILED DESCRIPTION OF THE PREFERRED EMBODIMENTS

Figure 1:
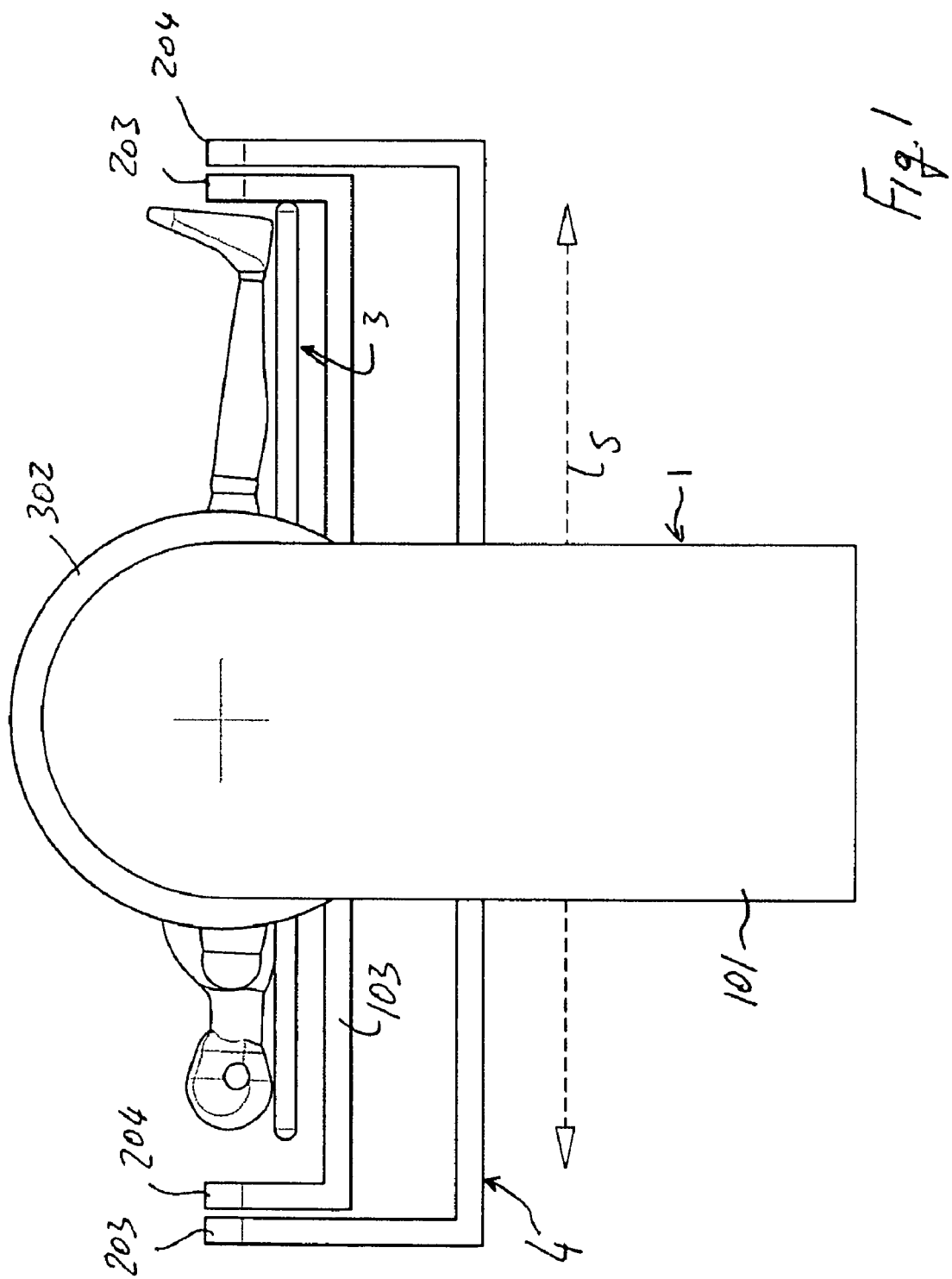
FIG. 1 is a lateral view of a preferred embodiment of the MRI apparatus according to the invention with the table having an horizontal position allowing to carry out imaging in particular but not only of the spine, of the knee and of the ankle.

An embodiment of an MRI imaging apparatus according to the present invention is schematically illustrated in FIGS. 1 to 9.

The MRI apparatus comprises a supporting basement 1 which is formed by two parallel vertical walls 101 which are spaced apart one from the other. Between the two vertical walls 101 a magnetic structure 2 is provided. The magnetic structure 2 is formed by an U-shaped yoke which is supported by the basement 1 between the two vertical walls 101. The U shaped yoke has a central transverse branch 102 and two lateral parallel branches 202. The central branch 102 is oriented horizontally and transversely to the two vertical walls of the supporting basement 1 and connects the two lateral branches 202 which lay in planes parallel to the two opposite vertical walls 101 of the supporting basement 1. At its the free end each lateral branch 202 of the U-shaped yoke bears a magnetic pole 302. The two magnetic poles are facing each other, being spaced apart one from the other and each one has a vertically aligned wall 402. The two spaced apart and facing walls of the two opposite poles 302 delimits laterally an imaging volume or space and are aligned along a central axis which is horizontal and transverse to the walls 402 of the poles 302 and/or to the walls 101 of the basement 1.

The U-shaped yoke of the magnetic structure 2 with the poles is supported rotatable at the upper ends of the vertical walls 101 of the basement. The axis of rotation is an horizontal axis which is parallel to an axis perpendicular to the two opposite walls 101 of the supporting basement 1, and or to the facing walls 402 of the two opposite poles 302 and which can also be parallel to the longitudinal axis of the central branch 201 of the yoke. In a preferred construction the poles 302, particularly the walls 402 of the poles 302 have a central axis which is perpendicular to both the said walls 402 and to the walls 101 of the basement 1 and which central axis coincides with the axis of rotation.

A table 3 is provided between the poles 302 of the magnetic structure. The table 3 is supported slidably relative to the magnetic poles along a direction which is parallel to its longitudinal axis as indicated by the arrow S on FIGS. 1 to 9. A first table supporting frame 4 has an elongated element 104 which is parallel to the central longitudinal axis of the table 3 and which is slidably mounted within a passage in the central horizontal branch 102 of the yoke. The translation of the elongated element 104 can be actuated with different devices, such as a motorized pinion associated to the yoke which is engaged with a rack secured to the elongated element 104. Alternatively the translation of the elongated element 104 relative to the yoke can be achieved by means of linear pneumatic or hydraulic actuators. This actuating devices are not shown in detail in the figures since they are generally known to the expert in the art and since the choice of a particular kind of translation actuator falls within the normal skill of the expert in the art.

The elongated, longitudinally oriented element 104 of the table supporting frame 4 is U shaped and at the free ends of the elongated element 104 projecting over both the transverse ends of the table 3 has respectively an angled, particularly perpendicular branch 204 which is directed in the rear/front direction of the table projecting over the table front side in a position in which the table is oriented perpendicularly to the walls 402 of the poles 302. The angled branches 204 of the table supporting frame 4 have a length which is greater than at least half of the width of the table 3. The table 3 is secured with its rear side to a further elongated element 103 which is parallel to the longitudinal axis of the table 3 and aligned with the central longitudinal axis of the table 3, The elongated element 103 terminate at the transverse ends of the table 3 and at these ends the elongated element 103 shows respectively an angled protrusion 203 which protrusions are oriented in the rear/frontal direction of the table. The protrusions 203 project over the front side of the table 3 and each one of the said protrusions 203 is supported rotatably around a common rotation axis which is parallel to the central longitudinal axis of the table 3 at a corresponding angled end branch 204 of the table supporting frame 4.

The rotation of the table around an axis which is parallel to its longitudinal central axis and of the yoke of the magnetic structure 2 with the poles 302 around an axis which is perpendicular to the longitudinal axis of the table can be achieved by means of conventional and known devices such as a motorized gear which cooperate with a toothed crown associated to the yoke in a position coaxial to the rotation axis of the magnetic structure 2 and a motorized gear which cooperates with a toothed crown associated to the table 3 and which is coaxial to the rotation axis of the table. Also a direct connection of a motor to the yoke or to the table is possible as well as the provision of transmissions with belts or the like. Also in this case the actuating device are not shown in the figures since these devices falls within the normal knowledge and skill of the expert in the art.

According to the above described construction of the MRI apparatus the table may be brought into different positions also relative to the magnetic poles 302. A first common rotation of the magnetic structure 2 with the entire yoke and the poles 302 and of the table supporting frame 4 with the table 3 around an horizontal axis which is perpendicular to the poles 302 and to the longitudinal axis of the table 3 is possible as clearly shown by the arrow R1 of FIGS. 3,4,5,7 and 9 is possible. The rotation allow to bring the table 3 from an horizontal position to a vertical position as shown in FIGS. 1 to 9.

Furthermore the table 3 can be rotated around its longitudinal central axis or an axis parallel to it according to the arrow R2 3, 4, 5, 7 and 9. Thus the table can be brought from a position in which it is substantially perpendicular to the walls 302 of the poles 302 in a position in which it is substantially parallel to the said walls 402 of the magnetic poles 302. Obviously this rotation has only a practical sense when the table is oriented vertically.

Further to the said rotations according to the two axis which are perpendicular one with respect to the other the table supporting frame can be further displaced along its longitudinal direction with respect to the magnetic structure 2 and to the poles 302. This displacement can be carried out irrespectively to the orientation of the table 3 along a vertical or an horizontal plane or along a plane which is intermediate to the said vertical and horizontal planes.

It has to be stressed that although not illustrated specifically, at one end the table 3 is provided with a foot rest. The footrest can be supported or formed by the corresponding protrusion 203 of the elongated element 103 secured to the table 3. Furthermore locking means may be provided for blocking the magnetic structure 2, the frame 4 and the table 3 in the different positions of rotation and in the different slide positions.

The different positions of the table 3 allow to carry out with the same MRI apparatus the imaging of a large number of different anatomic regions of the patient's body under different conditions such as stressed or unstressed.

Figure 2:
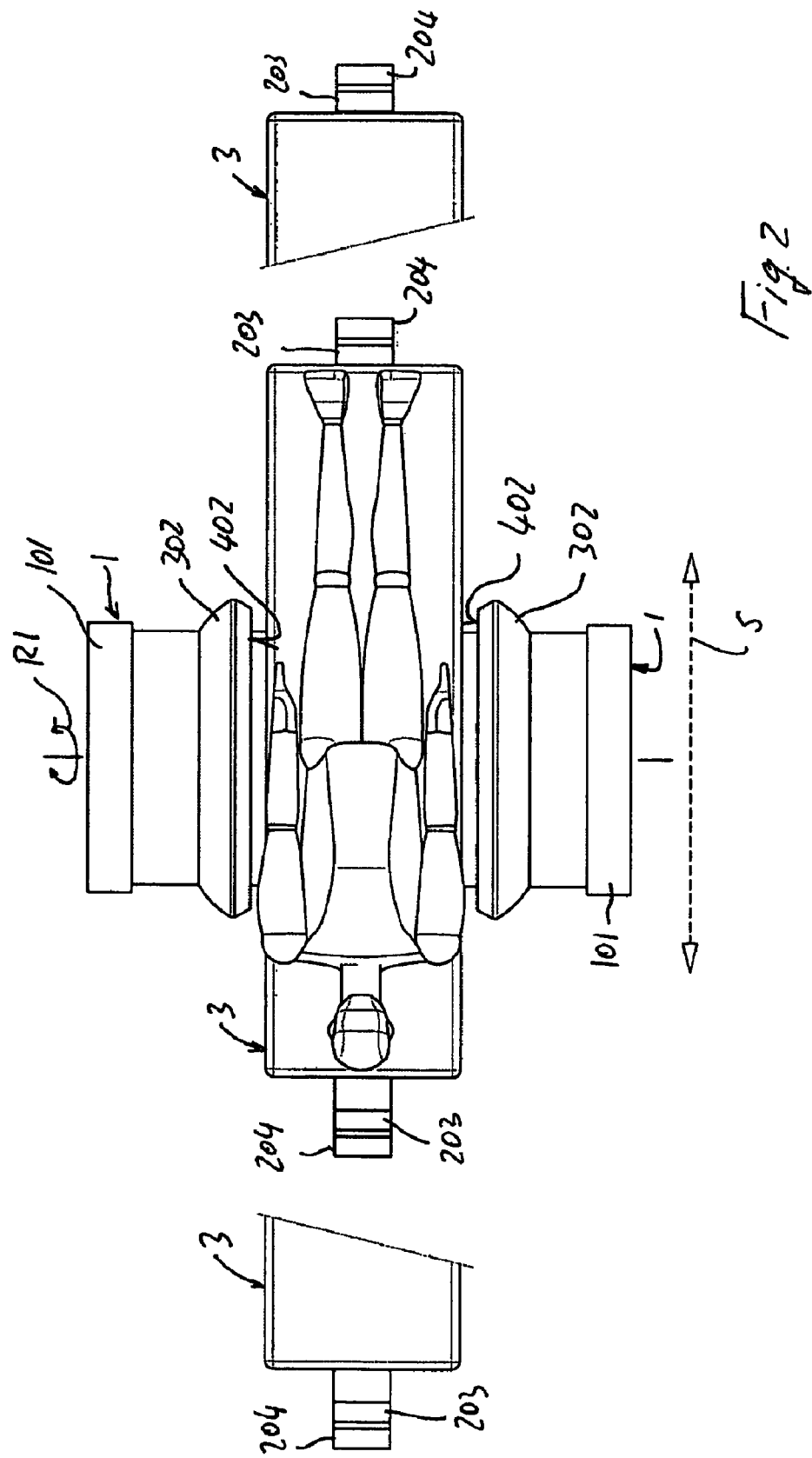
FIG. 2 is a top view of the apparatus according to FIG. 1, where the two end positions of the longitudinally slidable table are indicated.
Figure 3:
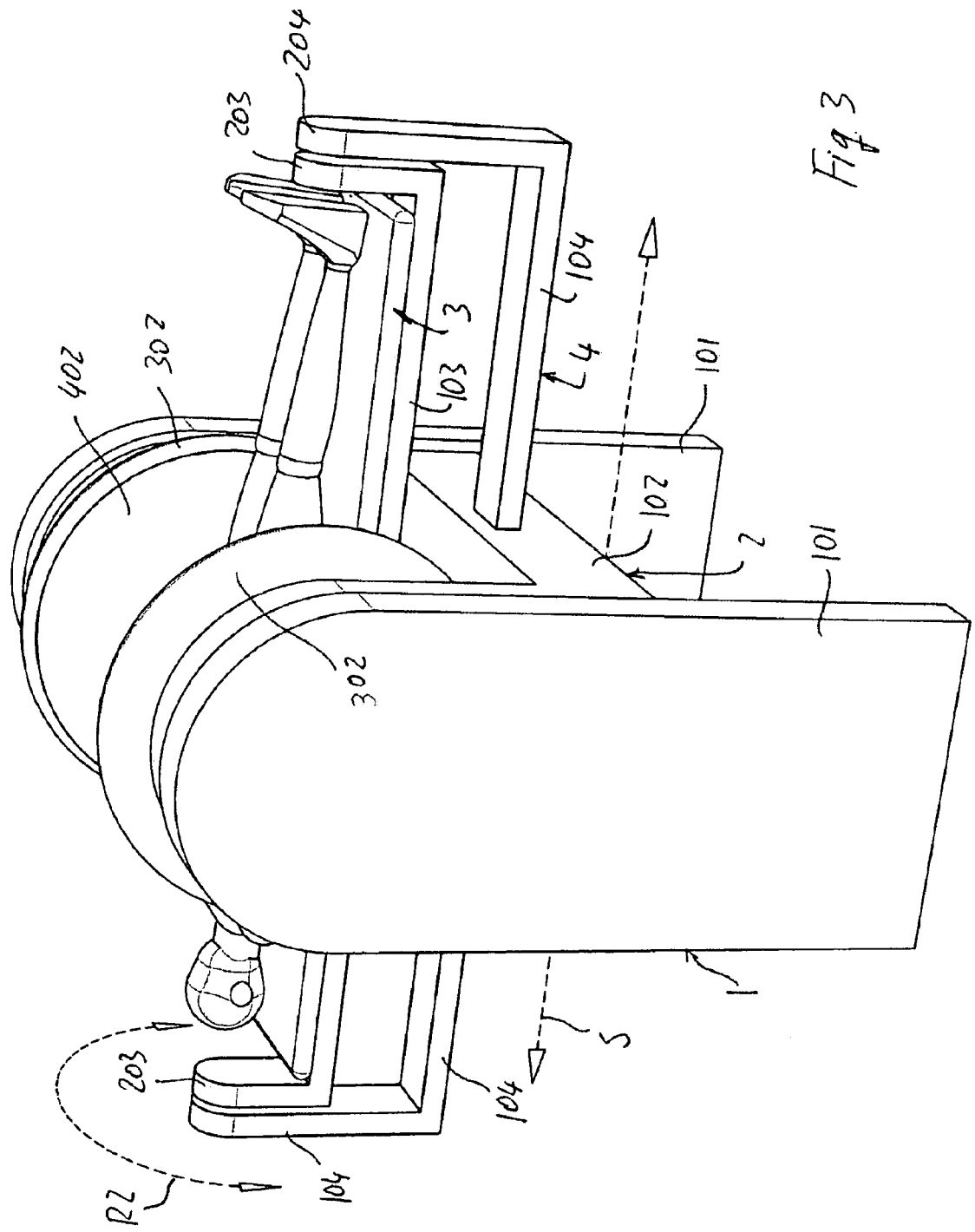
FIG. 3 is a perspective view of the apparatus according to FIGS. 1 and 2.
Figure 4:
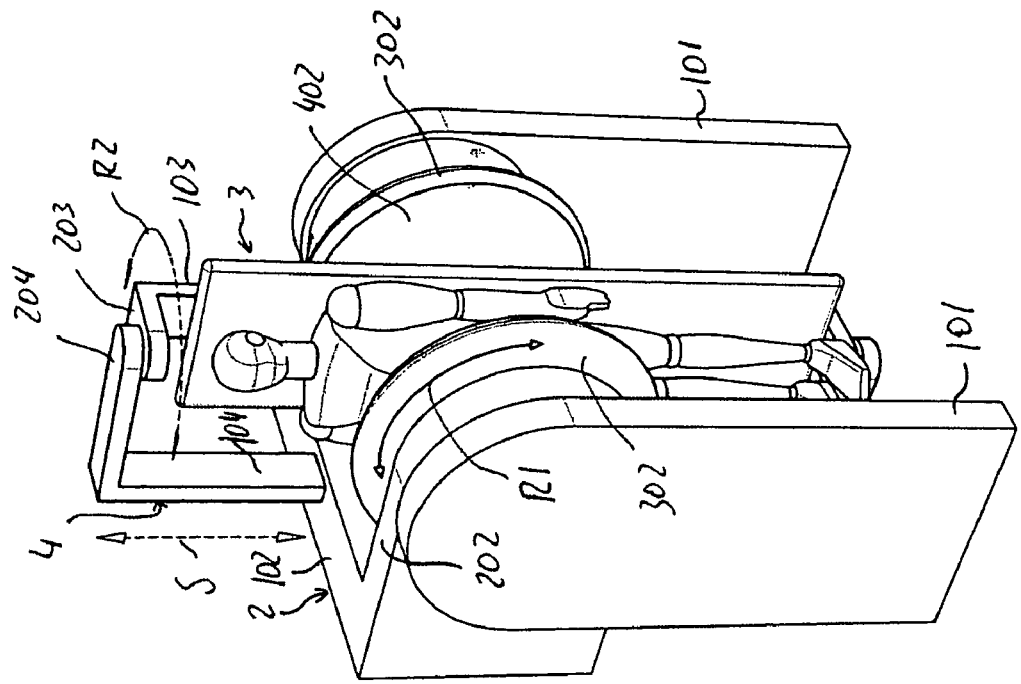
FIGS. 4 and 5 illustrate the MRI apparatus according to the present invention in which the table is oriented vertically and respectively parallel or perpendicular to the imaging volume defining walls of the poles of the magnetic structure, the position of FIG. 4 allowing imaging in particular but not only of the shoulder, the hands, the wrists, the elbow in an unstressed condition and of the hip under stress while the position of FIG. 5 allows imaging of the lumbar spine region and of the knee under stress.

In the horizontal position of the table 3 according to FIGS. 1 to 3 it is possible to carry out imaging of all parts of the spine, of the knee and of the ankle each one of the said anatomic district in an unstressed condition. The corresponding region of the spine, such as the cervical or lumbar region, the knee and the ankle can be centered relative to the imaging volume between the two poles 302 by sliding the table 3 with the frame 4 relative to the magnetic structure along the longitudinal direction of the table according to the arrow S.

Figure 5:
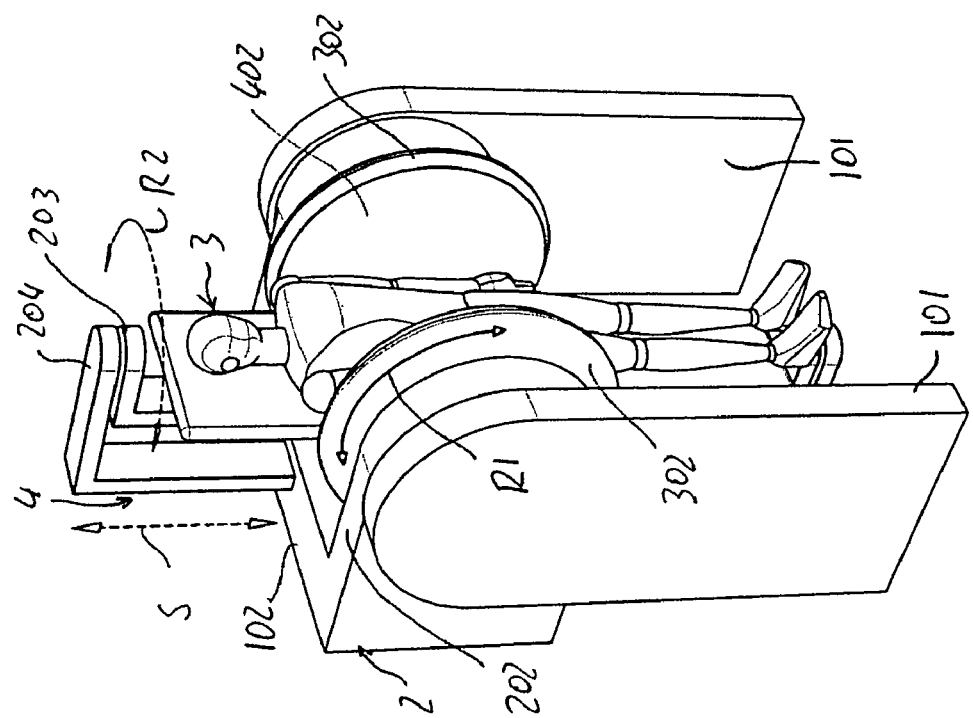
Figure 9:
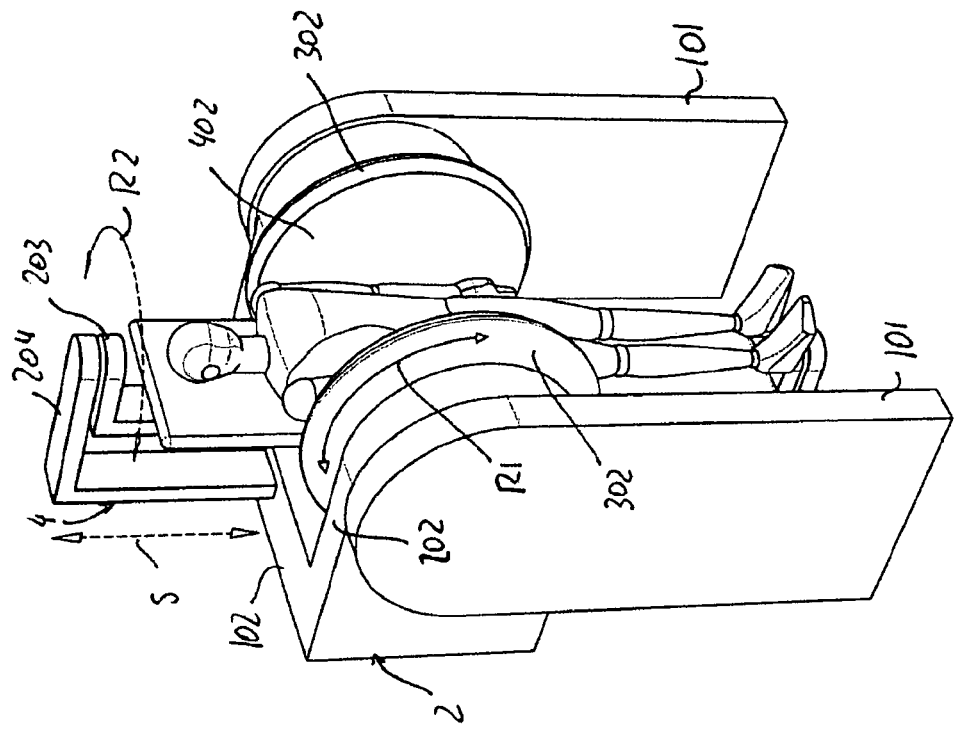
FIGS. 8 and 9 are a lateral view and a perspective view of the apparatus according to the present invention where the patient position allows respectively imaging in particular but not only of the knee under stress and of the lumbar region of the spine under stress.
Figure 8:
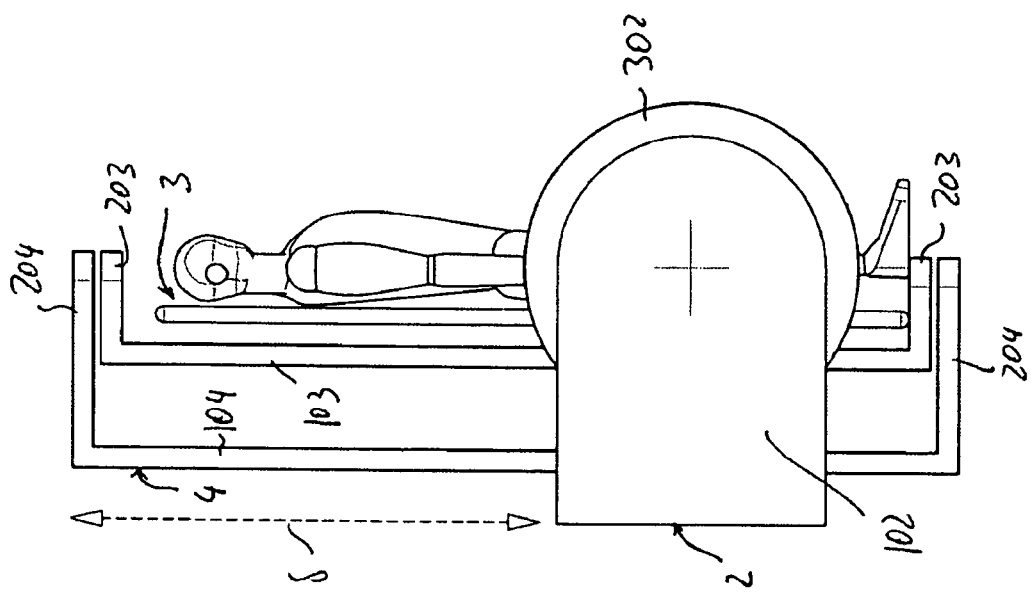

By rotating the table 3 from its horizontal position in a vertical position and maintaining the table 3 perpendicular to the walls 402 of the poles 302 or parallel to the horizontal rotation axis common to the table 3, to the table supporting frame 4 and to the magnetic structure 2, the table reaches the position according to FIGS. 5, 8 and 9. The table 3 may be further displaced along its longitudinal direction relative to the poles 302. This displacement can be carried out when the table 3 is still horizontal or even when the table 3 is vertical. In this condition the apparatus allows to carry out imaging in particular but not only of the following anatomical regions: lumbar spine under stress knee under stress depending on the longitudinal displacement of the table 3 relative to the poles 302. FIGS. 5 and 9 are the positions in which the imaging can be carried out particularly but not exclusively of the lumbar spine. FIG. 8 illustrates the position of the table relative to the magnetic structure 2 and the poles 302 in which the imaging can be carried out particularly but not only of the knee.

When the table is in its vertical position, the table 3 can be further rotated around its central longitudinal axis or an axis parallel to it taking the configuration illustrated in FIG. 5. In this configuration and depending on the displacement of the table along its longitudinal axis relative to the poles 302 particularly but not exclusively the following anatomical regions can be imaged: shoulder, hand, elbow, wrist in an unstressed condition and hip in a stressed condition.

According to another feature of the present invention which is illustrated schematically in FIGS. 6 and 7, the table 3 may be provided with a seat 5. The seat 5 can be mounted on the table 3 after the table has been positioned in the vertical position or the seat 5 can be formed by a seat plate which is hinged to the front side of the table 3 and can be swung from a position which is parallel to the table 3 in a position which is perpendicular to the table 3 and locked in this position. The seat plate can be also part of the table 3 which is formed in this case by at least two parts hinged together around an axis which is transverse to the table 3.

In the said vertical position of the table and with the seat mounted on the table or with the table transformed in a seat it is possible to carry out imaging particularly, but not exclusively of the cervical region of the spine in stressed condition.

According to a further embodiment, the table supporting frame and the table may be made of two parts hinged together around a transverse axis and inn such a manner that it allow the upper part of the table and of the supporting frame to be swung in an angled position relative to a lower part when the table is in its vertical position. In this condition illustrated in FIG. 10 the patient can lay down on the table in a prone posture. This allow to take images of the lumbar region of the spine in a stressed condition and with the patient in a position which can be less painless if the patient is afflicted by a spinal pathology.

Furthermore is has to be appreciated that the versatility of the MRI apparatus with respect to the positions that the patient may assume also helps to have enough free space for the medical personal to have access to the anatomical region imaged for carrying out any kind of interventions.

Providing that the distance of the poles 302 of the magnetic structure is greater than the width of the table, the table supporting frame 4 can also be provided with transverse slides at the angled branches 204 so that the table may also be displaced along its transverse axis.

The footrest 6 and the seat 5 are mounted on the table 3 or on the table supporting frame in such a way as to be slidable along the longitudinal direction of the table 3. Furthermore, alternatively or in combination, the footrest 6 and the seat 5 can also be mounted in such a way as to be swingable around an axis transversal, in particular perpendicular to the longitudinal axis of the table 3. Thus it is possible for the patient to take different postures during the imaging session for stressing in different ways anatomical districts such as the knee, the hip, the spine, etc. The slidable footrest 6 allows also to adapt the position of the patient relative to the imaging volume between the poles 302 of the magnetic structure depending on the anatomical district to be imaged or depending on the different heights of the patient. The combination of slidable seat 5 and footrest 6 and the different postures of the patient can be achieved therewith is illustrated in FIGS. 13 to 15. The footrest 6 and the seat 5 can be provided with releasable securing means so that they can be mounted on the table or on its supporting frame when needed or taken away when there is no need.

Particularly when the table and/or the magnetic structure are in the position in which the table 3 is not horizontal, especially substantially vertical, means are provided for supporting the patient in different postures.

According to a first example which is illustrated in FIGS. 10 to 12, the apparatus can be provided with knee supporting means 10. This means can be secured to whichever part of the apparatus, but preferably this knee supporting means are secured to the table 3 or to its supporting frame. In the embodiment shown in FIGS. 10 to 12, the knees supporting means 10 are in the form of a knee rest having a knee support 110 in the form of a plate which is oriented transversely to the longitudinal axis of the table 3 and which is provided at the end of one or two lateral arms 210 which opposite end is secured to the table 3 and/or to the table supporting frame. In one preferred embodiment the knee supporting means 10 are secured slidably along the longitudinal direction of the table 3. Alternatively or in combination the knee supporting means 10 can be supported also in a swingable way around an axis which is transversal in particular perpendicular to the longitudinal axis of the table 3. The knee support means can be provided alone or in combination with the footrest 6 or in combination with the seat 5 or in combination with both the footrest 6 and the seat 5.

As it becomes clear from FIGS. 10 to 12, the knee supporting means 10 in combination with the footrest 6 and/or with the seat 5 allows the patient to take different postures, particularly when the table is in a non horizontal or in a substantially vertical position. These postures allows to carry out imaging of various anatomical regions such as the knee, the spine, the hip, etc. in different stress conditions of the said anatomical regions.

Particularly the said combinations of knee rest 10, footrest 6 and seat 5 can help the patient to take a posture having the knees bent at different angles in a non horizontal position or in a substantially vertical position, i.e., in a substantially upright position of the patient.

Particularly, when the patient is in a substantially upright position, i.e. when the table is in a substantially vertical position where the table 3 is not perfectly vertical but is inclined more than 90° with respect to the horizontal plane and/or when the table 3 is made of two parts which can take different angular positions one with respect to the other and the upper part of the table is swung in a position having an angle which is more than 90° with respect to the horizontal plane, the apparatus according to the present invention provides for further patient supporting and/or retaining means which are illustrated in FIGS. 16 to 19. These different patient supporting and/or retaining means can be provided in any combination or sub combination and ore can be combined with one or more, or all the patient supporting and/or retaining means consisting in a footrest 6, a knee rest 10 and a seat 5, depending on the posture to be taken by the patient during the imaging session.

In FIG. 16 the patient supporting and/or retaining means are formed by an armrest 11 against which the patient can exercise a force by its arms pushing himself against the table 3. In the example illustrated in FIG. 16, the arm rest has a structure which is widely identical to the one of the knee rest 10 except for the fact that the knee supporting surface 110 is substituted by a grasping element 111 for the hands. This grasping element 111 is supported by one or two arms 211 each one at one side of the grasping element 111. The arms 211 can be regulated relative to their length for adapting the length of the arms of the patient and the supporting arm or arms 211 can be secured slidably along the longitudinal extension of the table 3, at least for part of this extension and/or swingably around a transversal axis, particularly a perpendicular axis with respect to the longitudinal axis of the table 3. In an embodiment for allowing a variation of the length of the supporting arms 211, these arms can be built as telescopic arms.

According to FIG. 17, a further patient supporting and/or retaining means is provided by a patient securing belt 12. The securing belt 12 illustrated in FIG. 17 is provided at the chest of the patient. Obviously more than one securing belt can be provided acting on different parts of the body of the patient. Similarly to the footrest, to the seat and to the knee rest and to the arm rest the belt can be secured in a releasable manner to the table 3 or to its supporting frame, being also possible to provide securing means which allow the belt to swing around an axis transverse, particularly perpendicular to the longitudinal axis of the table. Also in the case of the securing belt 12 the means for securing the belt to the table can be of the kind allowing to slide the belt in the longitudinal direction of the table 3.

Instead of being secured to the table 3 or to the table supporting frame with slidable means, the footrest 6, the seat 5, the knee rest 10, the arm rest 11 and the securing belts 12 may be provided with securing means to the table or to the table supporting frame which cooperates with a plurality of fastening points distributed over the table and/or over the table supporting frame, particularly over the length of the table supporting frame. Thus instead of a continuous regulation of the position a stepwise regulation of the position is provided.

Figure 19:
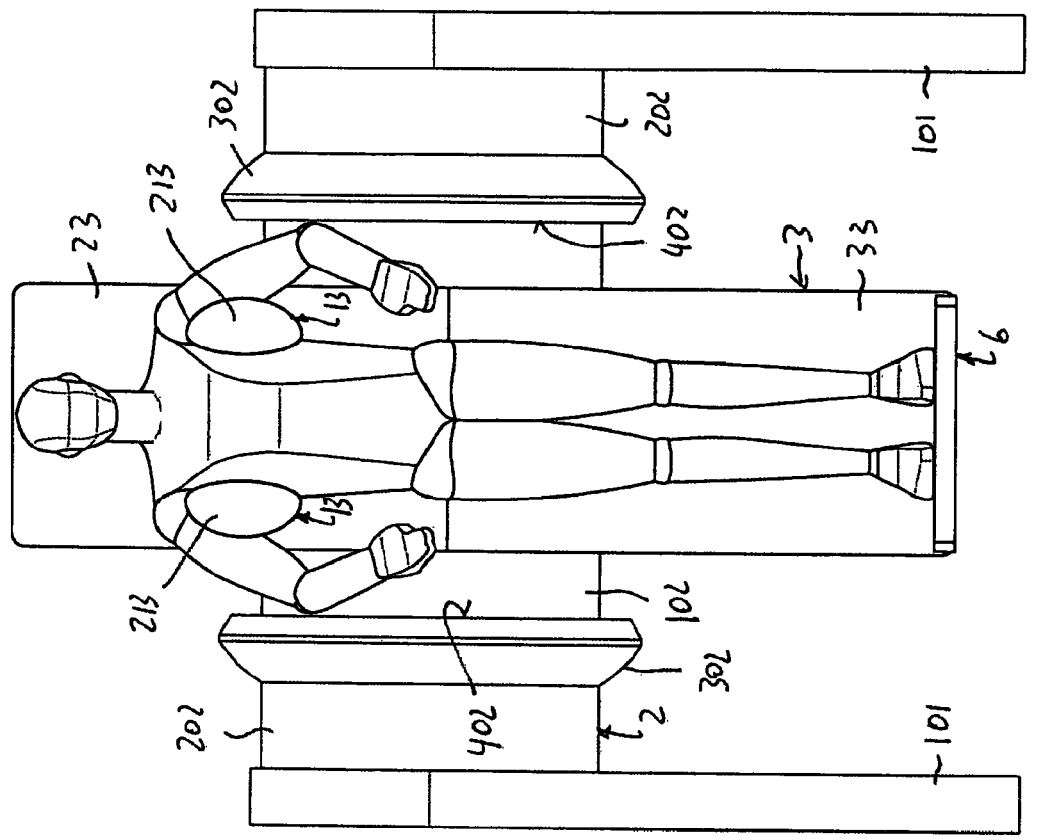
FIGS. 18 and 19 show a lateral and a frontal view of the apparatus in which the table is provided in combination with patient supporting and/or retaining means cooperating with the armpits of the patient.
Figure 18:
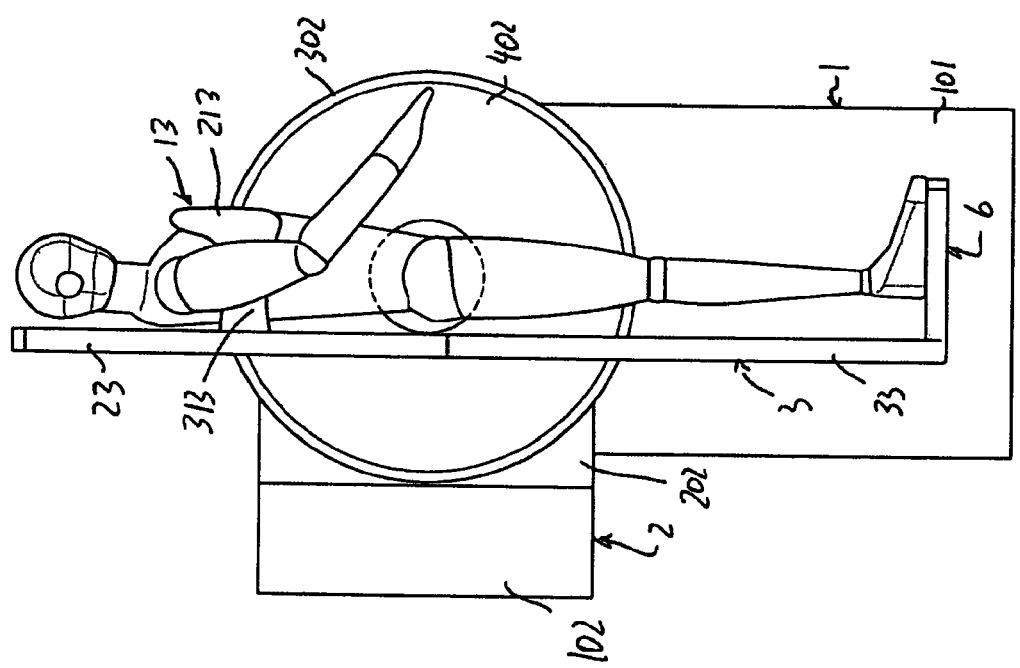

Another embodiment of the patient supporting and/or retaining means is illustrated in FIGS. 18 and 19. In this embodiment at least one, preferably two armpit supporting means 13 are provided. This are in the form of a bracket 113 secured to the table or to the table supporting frame in such a way to project substantially perpendicularly to the said table 3. The brackets have a rounded an elongated cross-section in the longitudinal direction of the table, forming a rest surface for the armpits which is anatomically shaped correspondingly to the armpits. At the free ends of the brackets 113 a laterally enlarged head 213 is provided which forms a rest surface for the frontal side of the arm and of the chest in the region surrounding the armpit. Also the said head is rounded in a way as to prevent hurting of the patient. Similarly to the other patient supporting and/or retaining means described above also the armpit supporting means 13 are secured in releasable way to the table or to the table supporting frame. The said armpit supporting means can also be slidable along the surface of the table at least in a longitudinal direction of the said table, preferably also in a direction transversal to the said longitudinal direction. Instead of being slidable the armpit supporting frames may be secured at different predetermined points on the table surface at which fastening points are provided. The armpit supporting means can also be secured in a way allowing to be inclined relative to the table 3 in one or both of the two direction defining the table 3.

According to a further improvement that allows the patient to be provided in a more simple and comfortable way with the armpit supporting means, the heads of this armpit supporting means can be mounted at the ends of the bracket either in a releasable manner or in such a way as to be rotated around an axis parallel or coincident with the axis of the corresponding bracket and/or in a way as to displaced in an eccentric position. Thanks to the above, the patient may take place on the table provided with the armpit supporting means in a more comfortable way being possible to mount the heads 213 after that the patient has taken place on the table 3 or to displace the heads 213 in a position in which the said heads do not impede seriously the placement of the patient. Obviously, it is also possible due to the releasable securing means of the armpit supporting means to the table to mount the said armpit supporting means only after that the patient has taken place on the table 3.

As already said with respect of the previously described patient supporting and/or retaining means, also the armpit supporting means can be provided in combination with one or more or with all the above described other patient supporting and/or retaining means as the footrest 6, the seat 5, the knee rest 10, the armrest 11 and the belt 12.

Relating to the means and mechanism for securing in a releasable way the different patient supporting and/or retaining means described above and/or for allowing the displacement of these patient supporting and/or retaining means along one or both directions defining the table 3 and/or for allowing the said patient supporting and/or retaining means to be further swung around a certain axis, these securing means and mechanisms are also provided with releasable means for locking the patient supporting and/or retaining means in potion once the positioning of the said patient supporting and/or retaining means in the desired position and orientation has been carried out.

The said securing means and mechanisms are obvious for the skilled person which can chose between a large number of constructive options being part of its basic technical knowledge.

A further embodiment which can be provided alone or in combination with one or more of the features described above as far as these are not contradictory, consists in the fact that the table 3 for positioning the patient is formed by at least two parts 23 and 33 which can be swung around at least one axis which is transverse, particularly perpendicular to the longitudinal axis of the table 3. An embodiment of the table is illustrated by an example in the FIGS. 20 to 24.

In the embodiment of FIGS. 20 to 24 the table 3 is provided of a table plate which is formed by two parts 23, 33 each part forming half of the entire length of the table plate. The two parts are hinged at a central axis H which is perpendicular to the longitudinal axis of the table 3. A frame 43 supports the table plate 23, 33 and is mounted slidably in guides 15 by means of slides 16 or roller mounted on the frame 43. The said slides or roller 16 are secured to the longitudinal sides of the frame 43 and two parallel longitudinal guides 15 are provided at coincident positions with the said longitudinal sides of the frame 43. The two guides 15 are directly mounted to the yoke, particularly to the transverse element 102 of the yoke connecting the two poles 302, which poles 302 and which transverse element 102 are rotatable together with the table 3 around an horizontal axis transverse to the longitudinal direction of the table 3 and substantially parallel to the transverse element 102.

According to a further feature the two longitudinal guides 15 can be mounted on a carriage which is slidably engaged in one or more guides oriented parallel to the transverse axis of the table 3 and/or to the axis of rotation of the magnetic structure 2 together with the table 3. These two further transverse guides can be secured to the transverse element 102 of the magnetic structure allowing the table also to be displaced in an eccentric position between the two opposite poles 302.

The swingable parts 23 and 33 of the table plate can be separately and independently angularly displaced one with respect to the other and relative to the frame 43 as it appears from FIG. 24, means being provided for angularly displacing the said parts 23 and 33 of the table plate and also for locking the two parts in a certain desired angular position. Said means can be provided as a manual mechanism where the angular displacement of the parts 23 and 33 of the table plate is carried out manually as well as the locking and unlocking the said parts in the desired angular position. Alternatively said means can be provided as a mechanism with actuators which carry out the angular displacement ad automatically sets free or locks the two parts 23 and 33 of the table plate in the desired angular position.

FIGS. 20 to 24 illustrate an example of a manually driven mechanism. Each part 23, 33 shows an independent frame 53 comprising at least two longitudinal elements which are parallel to the longitudinal sides of the frame 43. Each of the said longitudinal elements 53 of the frame of each part is connected by a lever 17 to the corresponding longitudinal side of the frame 43. The lever 17 is pivotally mounted on the inner side of the longitudinal side element of the frame 43, the axis of rotation being fixed with respect to the said element, while the other end is pivotally and slidably engaged with a longitudinal slot in the facing wall of the corresponding longitudinal element 53 of the frame of the part 23, 33 of the table plate. The slot 153 has one lower plane longitudinal edge, while the opposite edge is undulated forming thus a series of indention for engaging therein a connecting pin 18 carried by the associated end of the lever 17. Thus as it is shown by FIG. 24 the parts 23 and 33 of the table plate can be swung independently and locked temporarily in the desired angular position. The undulated edge can be shaped in any way, particularly in such a way as to ensure a stable engagement of the pin 18 particularly under of the weight of the patient.

Obviously further locking means can be provided and also different kind of mechanisms which construction can be chosen freely by the expert of the art form the different options provided by its common general knowledge.

The above described table can be used for further improving the number of different postures of the patient and of different stress conditions of the anatomical part to be imaged. Some examples are shown in FIGS. 25 to 34.

In the examples of FIGS. 25 to 28 and 34 at least the table 3 or the table frame 43 is rotated in a substantially vertical position. In these examples the table 3 and the magnetic structure 2 are rotatable together so that FIGS. 25 to 28 and 34 show also a rotated position of the magnetic structure 2 corresponding to the substantially vertical position of the table. From the figures it can be appreciated that it is possible to displace angularly only the lower part 33 of the table plate (FIGS. 25 and 26) or the upper part 23 of the table plate (FIGS. 27, 28 and 34). Furthermore FIGS. 25 and 26 shows two examples of posture of the patient where the lower part 33 of the table plate is displaced angularly upward. FIGS. 27 and 28 show postures of the patient obtained by displacing angularly downward and in the direction of the frontal side of the table plate the upper part 23 of the said table plate. As appears clearly from the FIGS. 25 to 28, the table plate into two parts 23 and 33 is provided in combination with an arm rest 13 and with a footrest 6.

FIG. 34 shows a posture of the patient obtained by displacing the upper part 23 of the table plate backward. In everyone of the FIGS. 24 to 28 and 34 the patient lays supine on the table.

FIGS. 29 and 30 show postures of the patient differing from the above mentioned ones principally for the fact that the patient lays prone on the table. The upper part 23 of the table plate is displaced in a similar way as in the FIGS. 27 and 28, but the footrest 6 is on the opposite side of the table plate as well as the patient.

The examples of FIGS. 31 to 33 show the table 3 and the magnetic structure 2 which are in the horizontal position. In FIG. 31, the lower or foot part 33 of the table plate is displaced angularly upward, while the upper part or the head part 23 is horizontal or substantially horizontal. In FIG. 32 also the upper or head part 23 of the table plate is displaced angularly upward. In FIG. 33, only the said upper or head part 23 of the table plate is displaced angularly upward while the lower or foot part 33 of the table plate is horizontal or substantially horizontal. In all three examples the patient lays supine on the table. Nevertheless similarly to the other examples of postures and depending on the angle between the two parts 23 and 33 of the table plate the patient may also lay prone on the table.

Although the various patient supporting and/or retaining means described above are provided secured or fastened to the table or to the table supporting frame, it is possible also to provide at least selected ones or all of the said patient supporting and/or retaining means which have fastening or securing means to the magnetic structure or to the machine frame supporting the magnetic structure.

Relating to the particular kind of table, having a table plate formed by two parts each of which is swingably hinged around an axis transverse to the longitudinal axis of the table, this kind of table may be provided also in combination with an MRI apparatus in which neither the magnetic structure, nor the table can be rotated, particularly in an MRI apparatus in which the table is substantially horizontal. In this case, since the various postures of the patient may bring the patient in positions in which patient supporting and/or retaining means are needed, the table and/or the magnetic structure and/or the machine frame are provided in combination with one or more of the above described patient supporting and/or retaining means.

It has to be noticed that referring to the table plate in to swingable parts, the two parts of the table and eventually of the table supporting frame being swingable in an angled position which angular width is comprised between an angle of more than 180° between the two parts particularly of more than 270° but slightly less than 360° and an angle of less than 90° but slightly more than 0° between the two parts, depending on the fact if the patient is laying on the table with its back or with its frontal side, i.e., in a prone or supine position.

A further embodiment of the apparatus according to the invention consist in a variant of the shape of the facing surfaces of the poles. Although the said poles are illustrated as having plane surfaces 402 defining an imaging volume, the apparatus according to the invention can be provided with poles which do not have plane surfaces 402. For example the poles may be provided with upstanding zones at the edges of the facing surfaces delimiting the imaging volume or with several protrusions which are due to elements for shimming the magnetic field between the said poles. In this case for a correct interpretation of the various orientation relative to the poles reference has to be made to an ideal mean surface or to an ideal pale surface enveloping the said not plane surfaces 402 of the poles.

From the above description it becomes clear that the apparatus according to the invention allows to carry out imaging of an anatomical region of the patient under different stress conditions. It is possible to carry out imaging in such a way as to provide sequences of different postures and load conditions of the patient at which of the said postures or sequences an imaging procedure is carried out thus it is possible to display the images in a time correct sequence with reference of the images acquired at the different postures of the patient. It is so possible to reveal how a pathologic condition may develop in combination with a motion of the patient leading to different postures and loads of the anatomic region.

This kind of analysis may be also correlated with inputs given by the patient relating to the pain level suffered by the patient at the different positions and postures or loads. Thus it is possible to better appreciate the pathology of the patient.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. A magnetic resonance imaging apparatus comprising:
a magnetic structure having two opposite and spaced apart poles and a column or wall transverse to the poles and connecting the poles; the poles defining two opposite walls delimiting a patient-imaging space, the two opposite walls extending along substantially parallel planes which are substantially parallel to a vertical plane; the magnetic structure further comprising a magnetic structure supporting basement having two lateral walls to which the magnetic structure is rotatably connected at a rotation axis of the poles; the poles being provided at two opposite free ends of a U-shaped yoke, a central branch of the yoke being oriented horizontally and substantially parallel to the rotation axis, which central branch of the U-shaped yoke supports the table supporting frame in a slidable way along a longitudinal direction of the table; the two opposite free ends of the U-shaped yoke support the poles and are hinged around a common axis of rotation to the lateral walls of the supporting basement of the magnetic structure; and
a patient positioning table which is slidably connected to a table supporting frame between the two poles; the table supporting frame being supported by the magnetic structure;
the table being positioned with its longitudinal axis substantially parallel to the two opposite parallel walls of the poles and the table being oriented with its transverse axis substantially perpendicular to at least one of the two opposite walls; the table being slidable with respect to the magnetic structure in a direction parallel to a longitudinal axis of the table; manual or automatic means being provided for displacing the table relative to the magnetic structure along the longitudinal axis;
a lock for locking the table in a selected position relative to the magnetic structure;
manual or automatic means being provided for rotating the frame about the longitudinal axis; the frame with the table and the magnetic structure being rotatable together from a position in which the table is substantially horizontal to a position in which the table is substantially vertical, and vice versa;
wherein the entire magnetic structure is supported rotatably together with the table supporting frame around the same axis, wherein the axis of rotation of the table supporting frame and of at least the poles of the magnetic structure substantially coincides with a central axis of the poles;
wherein the table supporting frame is formed by an elongated element slidably engaged with a central branch of a U-shaped magnetic yoke; the table supporting frame has also an U shaped form with the central branch extending in a longitudinal direction of the table and with a plurality of angled end branches projecting from the central branch in a measure which is greater than a half width of the table while both transverse ends of the table are rotatably secured around a common axis of rotation at free ends of the angled end branches of the table supporting frame; and
wherein the table is secured to a second table supporting frame which is also U-shaped; the second supporting frame having an elongated central branch directly secured to a rear side of the table and which end branches project forward at both transverse ends of the table; the end branches of the second table supporting frame having a length which is shorter relative to a length of the end branches of the table supporting frame and being rotatably secured with their ends to free ends of the end branches of the table supporting frame.

2. The magnetic resonance imaging apparatus according to claim 1, in which the table supporting frame being further supported rotatably along a central horizontal axis perpendicular to at least one or both of the two opposite walls of the poles relative to the magnetic poles or to the said magnetic structure at least for a limited angular displacement.

3. The magnetic resonance imaging apparatus according to claim 1, wherein the table has a table plate and is further provided with at least one seat plate which is swingable from a position parallel to the table plate into a position perpendicular to the table plate and vice versa and in which swung position part of the table plate forms a back of a seat.

4. The magnetic resonance imaging apparatus according to claim 3, wherein the seat plate is formed by a part of the table plate the table plate being formed by at least to parts hinged together at least one of which forms the swingable seat plate.

5. The magnetic resonance imaging apparatus according to claim 1, wherein a table plate and eventually the table supporting frame are formed at least by two parts which are hinged together along a transversal axis of the plate at least one or both of the two parts of the table and eventually of the table supporting frame being swingable in an angled position.

6. The magnetic resonance imaging apparatus according to claim 5, wherein the two parts of the table and eventually of the table supporting frame being swingable in an angled position which angular width is comprised between an angle of more than 180° between the two parts particularly of more than 270° but slightly less than 360° and an angle of less than 90° but slightly more than 0° between the two parts, depending on the fact if a patient is laying on the table with its back or with its frontal side, i.e., in a prone or supine position.

7. The magnetic resonance imaging apparatus according to claim 6, wherein the two parts of the table and eventually of the table supporting frame being swingable in an angled position which angular width is of substantially 270° or 90° depending on the fact if the patient is laying on the table with its back or with its frontal side, i.e., in a prone or supine position, particularly a position in which the table has a vertical part and an horizontal part which works as a support for the patient in a bend forward position.

8. The magnetic resonance imaging apparatus according to claim 1, wherein means are provided for rotating continuously or stepwise the table or the table supporting means or the poles or the magnetic structure.

9. The magnetic resonance imaging apparatus according to claim 1, further comprising: an angular locking means for locking the table or the table supporting frame or the poles or the magnetic structure in an angular position which is intermediate between a horizontal position and a vertical position or in an angular position which is beyond the horizontal position or over the vertical position.

10. The magnetic resonance imaging apparatus according to claim 1, wherein it is provided with a footrest which is fastened to or integral with a table plate or the table supporting frame.

11. The magnetic resonance imaging apparatus according to claim 1, wherein a footrest or a seat plate may be supported on the table or on the table supporting frame by means of a guide allowing the footrest or a seat to slide along the table or along the table supporting frame in both direction parallel to the longitudinal axis of the table or of the table supporting frame.

12. The magnetic resonance imaging apparatus according to claim 1, wherein a footrest and or a seat plate are pivotally supported on the table or on the table supporting frame around an axis which is transversal particularly perpendicular to the longitudinal axis of the table.

13. The magnetic resonance imaging apparatus according to claim 1, wherein the table or the table supporting frame or the magnetic structure or a machine frame are provided with means for retaining a patient against the table in different positions thereof, wherein the patient retaining means include one or more removable fastening belts of the patient against the table and the patient fastening belts are adjustable relating to their length.

14. The magnetic resonance imaging apparatus according to claim 1, wherein the table or the table supporting frame or the magnetic structure or a machine frame are provided with means for retaining a patient against the table in different positions thereof and the patient retaining means include armpit supporting means, i.e., means for supporting the patient cooperating with armpits of the patient.

15. The magnetic resonance imaging apparatus according to claim 1, wherein the table or the table supporting frame or the magnetic structure or a machine frame are provided with means for retaining a patient against the table in different positions thereof and the patient retaining means include knee retaining means against which the patient can push his knees or leg in order to exercise a force helping to maintain a position adherent to the table.

16. The magnetic resonance imaging apparatus according to claim 1, wherein the table or the table supporting frame or the magnetic structure or a machine frame are provided with means for retaining a patient against the table in different positions thereof and the patient retaining means include arm rests, in the form of handles against which the patient can exercise with his arms a force helping to maintain a position adherent to the table.

17. The magnetic resonance imaging apparatus according to claim 1, wherein the table or the table supporting frame or the magnetic structure or a machine frame are provided with means for retaining a patient against the table in different positions thereof and the patient retaining means are secured slidable along the table or the table supporting frame in a longitudinal direction thereof or in a transversal direction thereof.

18. The magnetic resonance imaging apparatus according to claim 1, wherein the table or the table supporting frame or the magnetic structure or a machine frame are provided with means for retaining a patient against the table in different positions thereof and the table, or the table supporting frame or the poles or the magnetic structure or the machine frame are provided with several fastening points of the patient retaining means which fastening points are distributed over a predetermined range of different positions and at which the patient retaining means are secured by means of releasable securing means.

19. The magnetic resonance imaging apparatus according to claim 1, wherein the table or the table supporting frame or the magnetic structure or a machine frame are provided with means for retaining a patient against the table in different positions thereof and the patient retaining means are secured to the table, or the table supporting frame or the poles or the magnetic structure or the machine frame in an angularly displaceable way, particularly around an axis which is transversal in particular perpendicular to the longitudinal axis of the table.

20. The magnetic resonance imaging apparatus according to claim 1, wherein the table or the table supporting frame or the magnetic structure or a machine frame are provided with means for retaining a patient against the table in different positions thereof and a knee retaining means, arm rests and an armpit supporting means are adjustable relating to their distance from the table or from the table supporting frame.

21. The magnetic resonance imaging apparatus according to claim 1, wherein the table or the table supporting frame or the magnetic structure or a machine frame are provided with means for retaining a patient against the table in different positions thereof and the patient retaining means, a footrest, a seat, swingable parts of the table plate are provided with releasable locking means for releasable locking them in position.

* * * * *